(12) United States Patent
Ghosh et al.

(10) Patent No.: US 8,694,099 B2
(45) Date of Patent: *Apr. 8, 2014

(54) CRITERIA FOR OPTIMAL ELECTRICAL RESYNCHRONIZATION DERIVED FROM MULTIPOLAR LEADS OR MULTIPLE ELECTRODES DURING BIVENTRICULAR PACING

(75) Inventors: Subham Ghosh, Circle Pines, MN (US); Robert W. Stadler, Shoreview, MN (US)

(73) Assignee: Medronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/464,279

(22) Filed: May 4, 2012

(65) Prior Publication Data
US 2013/0218227 A1 Aug. 22, 2013

Related U.S. Application Data

(60) Provisional application No. 61/600,462, filed on Feb. 17, 2012.

(51) Int. Cl.
*A61N 1/00* (2006.01)

(52) U.S. Cl.
USPC ......... 607/28; 607/9; 607/17; 607/25; 607/27

(58) Field of Classification Search
USPC .................. 607/9, 17, 25, 27, 28; 600/374
See application file for complete search history.

(56) References Cited

U.S. PATENT DOCUMENTS

| | | | |
|---|---|---|---|
| 4,940,052 A * | 7/1990 | Mann et al. | 607/17 |
| 6,606,516 B2 * | 8/2003 | Levine | 607/9 |
| 6,795,732 B2 * | 9/2004 | Stadler et al. | 607/17 |
| 7,239,913 B2 * | 7/2007 | Ding et al. | 607/9 |
| 7,289,850 B2 * | 10/2007 | Burnes et al. | 607/9 |
| 7,637,867 B2 * | 12/2009 | Zdeblick | 600/300 |
| 7,702,390 B1 | 4/2010 | Min | |
| 7,787,951 B1 * | 8/2010 | Min | 607/17 |
| 7,917,214 B1 * | 3/2011 | Gill et al. | 607/9 |
| 7,941,217 B1 * | 5/2011 | Pei et al. | 607/9 |
| 8,010,194 B2 * | 8/2011 | Muller | 607/14 |

(Continued)

FOREIGN PATENT DOCUMENTS

WO WO 2005/089867 A1 9/2005

OTHER PUBLICATIONS (PCT/US2013/026425) PCT Notification of Transmittal of the International Search Report and the Written Opinion of the International Searching Authority.

(Continued)

*Primary Examiner* — Niketa Patel
*Assistant Examiner* — Christopher A Flory
(74) *Attorney, Agent, or Firm* — Carol F. Barry

(57) ABSTRACT

Generally, the disclosure is directed one or more methods or systems of cardiac pacing employing a right ventricular electrode and a plurality of left ventricular electrodes. Pacing using the right ventricular electrode and a first one of the left ventricular electrodes and measuring activation times at other ones of the left ventricular electrodes. Pacing using the right ventricular electrode and a second one of the ventricular electrodes and measuring activation times at other ones of the left ventricular electrodes. Employing sums of the measured activation times to select one of the left ventricular electrodes for delivery of subsequent pacing pulses.

41 Claims, 10 Drawing Sheets

(56) References Cited

U.S. PATENT DOCUMENTS

| | | | |
|---|---|---|---|
| 8,036,743 B2* | 10/2011 | Savage et al. | 607/5 |
| 8,126,552 B2* | 2/2012 | Min | 607/17 |
| 8,155,739 B2* | 4/2012 | Keel et al. | 607/9 |
| 8,160,700 B1* | 4/2012 | Ryu et al. | 607/9 |
| 8,175,707 B1* | 5/2012 | Wright et al. | 607/18 |
| 2003/0100925 A1* | 5/2003 | Pape et al. | 607/17 |
| 2004/0106958 A1* | 6/2004 | Mathis et al. | 607/11 |
| 2005/0038478 A1* | 2/2005 | Klepfer et al. | 607/9 |
| 2005/0149138 A1* | 7/2005 | Min et al. | 607/27 |
| 2007/0129762 A1* | 6/2007 | Worley | 607/9 |
| 2008/0058656 A1* | 3/2008 | Costello et al. | 600/508 |
| 2008/0294218 A1* | 11/2008 | Savage et al. | 607/30 |
| 2009/0299423 A1* | 12/2009 | Min | 607/9 |
| 2010/0121397 A1* | 5/2010 | Cholette | 607/17 |
| 2010/0145405 A1 | 6/2010 | Min et al. | |
| 2010/0152801 A1* | 6/2010 | Koh et al. | 607/9 |
| 2010/0204593 A1* | 8/2010 | Park et al. | 600/508 |
| 2010/0268059 A1 | 10/2010 | Ryu et al. | |
| 2011/0022110 A1* | 1/2011 | Min | 607/25 |
| 2011/0022112 A1* | 1/2011 | Min | 607/25 |
| 2011/0066201 A1* | 3/2011 | Rosenberg et al. | 607/17 |
| 2011/0066202 A1* | 3/2011 | Rosenberg et al. | 607/17 |
| 2011/0066203 A1* | 3/2011 | Rosenberg et al. | 607/17 |
| 2011/0098770 A1* | 4/2011 | Ryu et al. | 607/25 |
| 2011/0098772 A1* | 4/2011 | Min | 607/28 |
| 2011/0118803 A1* | 5/2011 | Hou et al. | 607/17 |
| 2011/0137369 A1* | 6/2011 | Ryu et al. | 607/27 |
| 2011/0137639 A1* | 6/2011 | Yu et al. | 704/9 |
| 2011/0257697 A1* | 10/2011 | Jarverud | 607/18 |
| 2011/0319953 A1 | 12/2011 | Reed et al. | |
| 2011/0319954 A1* | 12/2011 | Niazi et al. | 607/17 |
| 2013/0218224 A1* | 8/2013 | Ghosh et al. | 607/28 |
| 2013/0218225 A1* | 8/2013 | Ghosh et al. | 607/28 |
| 2013/0218226 A1* | 8/2013 | Ghosh et al. | 607/28 |

OTHER PUBLICATIONS (PCT/US2013/026399) PCT Notification of Transmittal of the International Search Report and the Written Opinion of the International Searching Authority.

(PCT/US2013/026366) PCT Notification of Transmittal of the International Search Report and the Written Opinion of the International Searching Authority.

* cited by examiner

CRITERIA FOR OPTIMAL ELECTRICAL RESYNCHRONIZATION DERIVED FROM MULTIPOLAR LEADS OR MULTIPLE ELECTRODES DURING BIVENTRICULAR PACING

CROSS-REFERENCE TO RELATED APPLICATIONS

This application claims the benefit of U.S. Provisional Application No. 61/600,462, filed on Feb. 27, 2012. The disclosure of the above application is incorporated herein by reference in its entirety.

FIELD

The present disclosure relates to implantable medical devices (IMDs), and, more particularly, to selecting an optimal left ventricular electrode on a medical electrical lead extending from an IMD to deliver cardiac therapy delivery.

BACKGROUND

Implantable medical devices (IMD) are capable of utilizing pacing therapies, such as cardiac resynchronization therapy (CRT), to maintain hemodynamic benefits to patients. Pacing therapy may be delivered from an implantable generator, through a lead, and into the patient's heart. There are many ways in which to optimize a pacing configuration. CRT therapy involves biventricular pacing which consists of pacing the right ventricle (RV) with a RV electrode and a left ventricle (LV) with a LV electrode or monoventricular pacing which consists of pacing only the left ventricle. US Patent Publication 2011/0137639 by Ryu et al. discloses that the optimal left ventricle electrode is selected based upon conduction velocities. Another U.S. Pat. No. 7,917,214 to Gill et al. discloses that the optimal left ventricle electrode is selected based upon activation times and ARI dispersions. It is desirable to develop additional methods to optimize biventricular pacing.

DETAILED DESCRIPTION OF EXEMPLARY EMBODIMENTS

Figure 1:
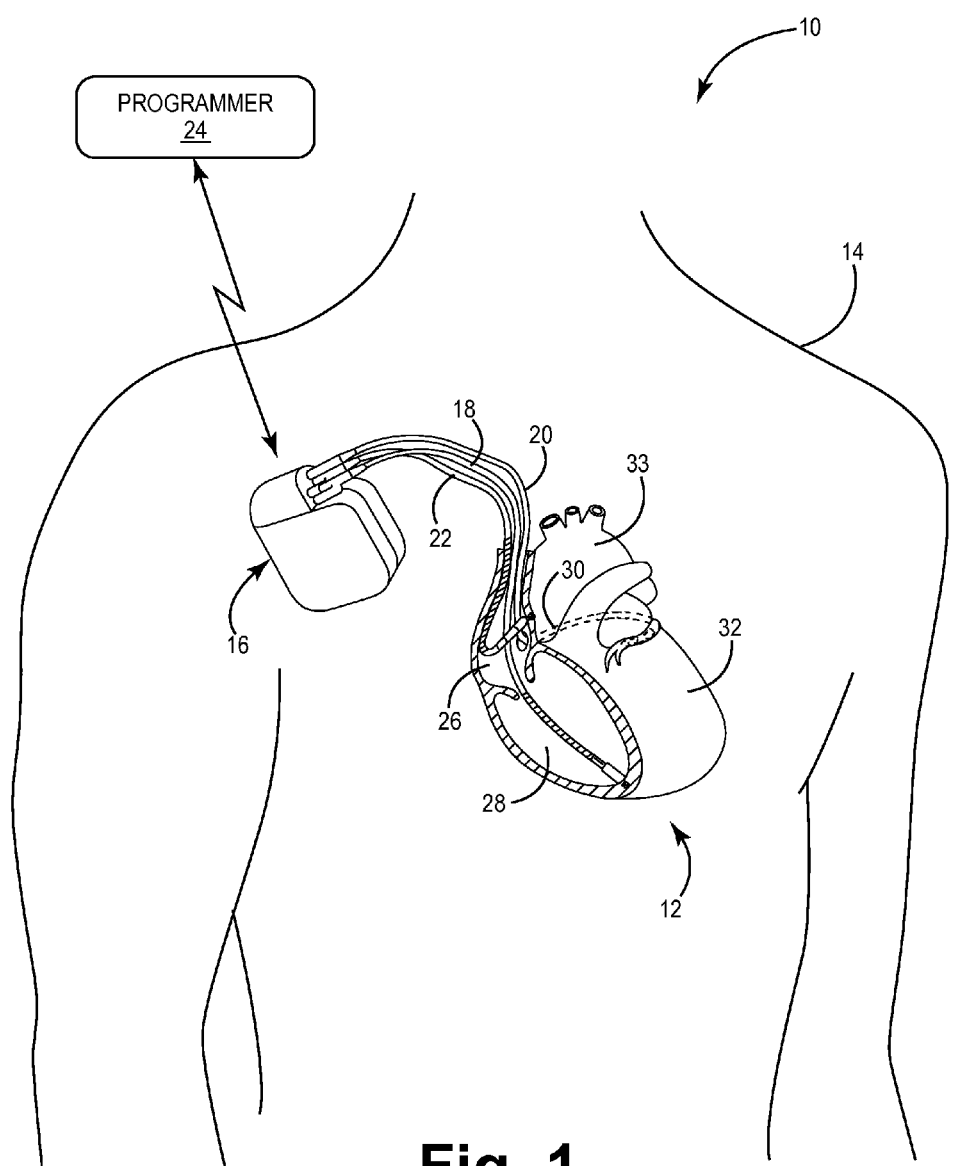
FIG. 1 is a schematic diagram of an exemplary system including an exemplary implantable medical device (IMD).

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

As described herein, a physician implanting a medical device can use criteria, stored in a programmer, to automatically select optimized location(s) and/or parameters for delivery of cardiac resynchronization therapy (CRT). For example, criteria can be used to determine an optimal left ventricular electrode from which electrical stimuli is delivered to the left ventricle. After the optimal LV electrode has been selected, other criteria can be used to optimize an atrioventricular delay, and/or an inter-ventricular delay for maximal cardiac resynchronization. Implementation of teachings of this disclosure can potentially improve cardiac resynchronization therapy (CRT) response in patients.

Exemplary methods, devices, and systems are described with reference to FIGS. 1-8. It is appreciated that elements or processes from one embodiment may be used in combination with elements or processes of the other embodiments, and that the possible embodiments of such methods, devices, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

FIG. 1 is a conceptual diagram illustrating an exemplary therapy system 10 that may be used to deliver pacing therapy to a patient 14. Patient 14 may, but not necessarily, be a human. The therapy system 10 may include an implantable medical device 16 (IMD), which may be coupled to leads 18, 20, 22 and a programmer 24. For the sake of brevity, programmer 24 includes a computer capable of the functions represented in FIG. 4 that are incorporated herein.

The IMD 16 may be, e.g., an implantable pacemaker, cardioverter, and/or defibrillator, that provides electrical signals to the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 1, the right ventricular (RV) lead 18 extends through one or more veins (not shown), the superior vena cava (not shown), and the right atrium 26, and into the right ventricle 28. The left ventricular coronary sinus lead 20 extends through one or more veins, the vena cava, the right atrium 26, and into the coronary sinus 30 to a region adjacent to the free wall of the left ventricle (LV) 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., pulse width, amplitude, voltage, burst length, etc. Further, the IMD 16 may be operable to use various electrode configurations to deliver pacing therapy, which may be unipolar or bipolar. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

In some examples, a programmer 24, which may be a handheld computing device or a computer workstation, may be used by a user, such as a physician, technician, another clinician, and/or patient, to communicate with the IMD 16 (e.g., to program the IMD 16). For example, the user may interact with the programmer 24 to retrieve information concerning one or more detected or indicated faults associated within the IMD 16 and/or the pacing therapy delivered therewith. The IMD 16 and the programmer 24 may communicate via wireless communication using any techniques known in the art. Examples of communication techniques may include, e.g., low frequency or radiofrequency (RF) telemetry, but other techniques are also contemplated.

Figure 2:
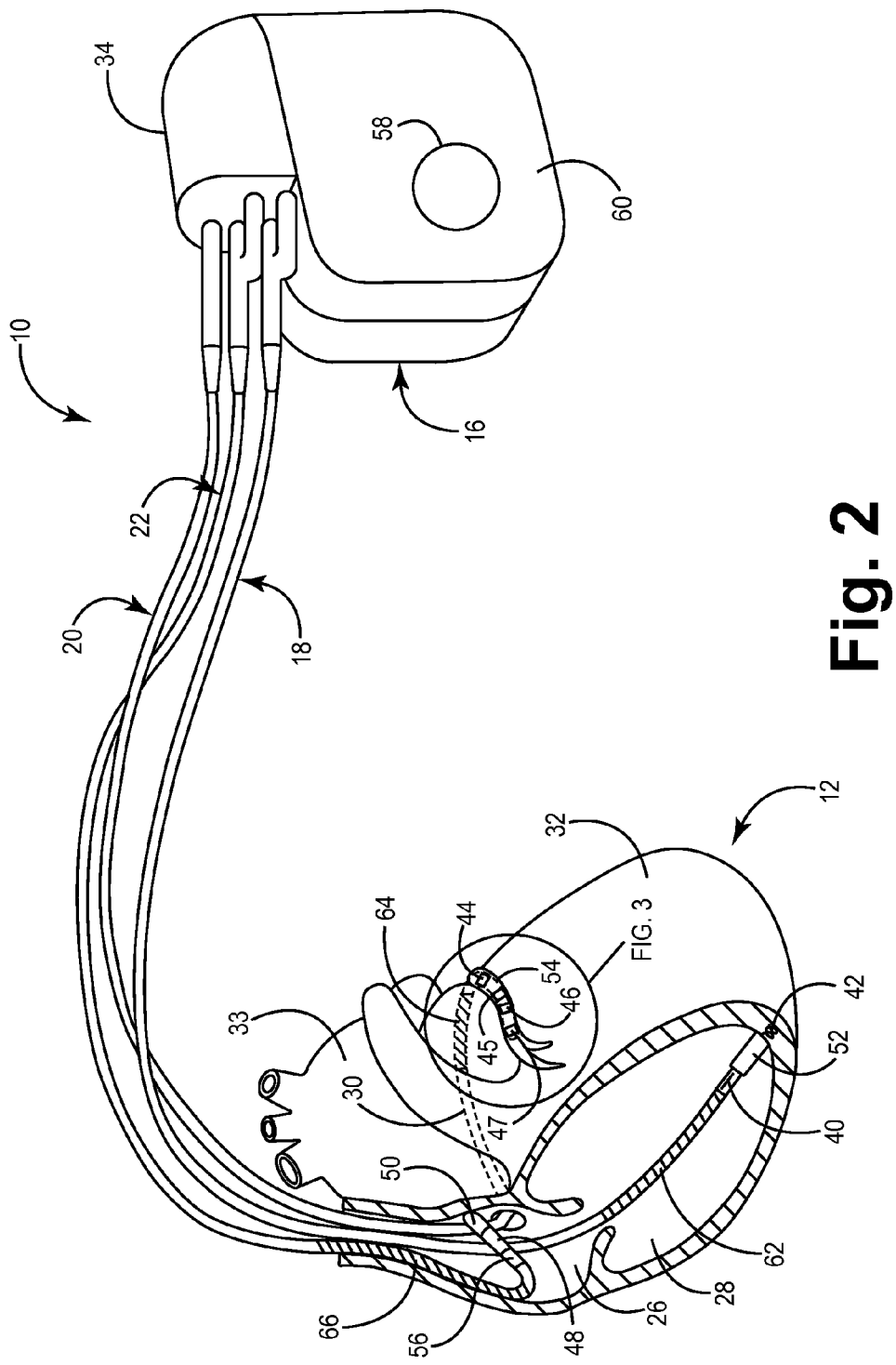
FIG. 2 is a schematic diagram of the exemplary IMD of FIG. 1.

FIG. 2 is a conceptual diagram illustrating the IMD 16 and the leads 18, 20, 22 of therapy system 10 of FIG. 1 in more detail. The leads 18, 20, 22 may be electrically coupled to a therapy delivery module (e.g., for delivery of pacing therapy), a sensing module (e.g., one or more electrodes to sense or monitor electrical activity of the heart 12 for use in determining effectiveness of pacing therapy), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths).

Exemplary leads that can be useful for the present disclosure include U.S. Pat. Nos. 5,922,014, 5,628,778, 4,497,326, 5,443,492, 7,860,580 or US Patent Application 20090036947 filed Apr. 30, 2008 such that electrodes are added and/or spaced apart in a manner similar to that disclosed in the figures of the present application, all of listed patents and applications are incorporated by reference in their entirety. Additional lead and electrode configurations that may be adapted for use with the present disclosure by adjusting lead shape, length, electrode number and/or electrode to effectively avoid phrenic nerve stimulation as described herein are generally disclosed in U.S. Pat. Nos. 7,031,777, 6,968,237, and US Publication No. 2009/0270729, all of which are incorporated herein by reference in their entirety. Moreover, U.S. Pat. No. 7,313,444, incorporated by reference, discloses a LV pacing lead such that the LV electrodes are about equally spaced, which could also be used to implement the present disclosure.

Figure 3:
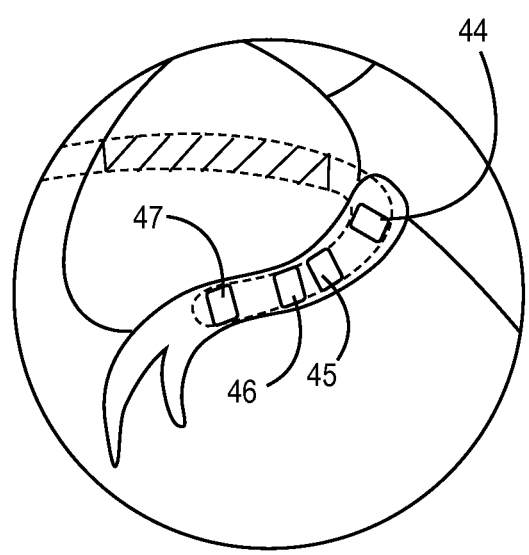
FIG. 3-3A are schematic diagrams of an enlarged view of a distal end of a medical electrical lead disposed in the left ventricle.
Figure 3A:
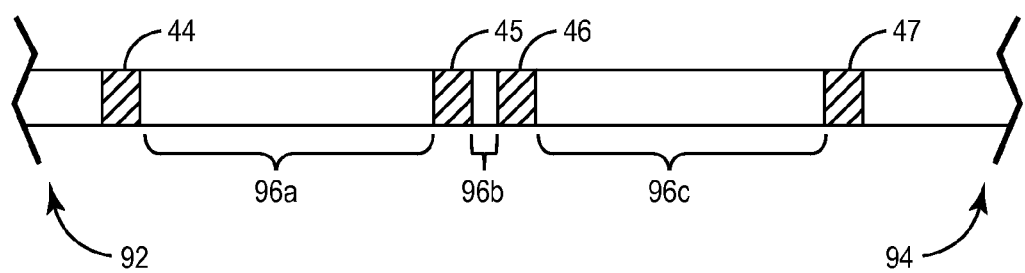

In the illustrated example, bipolar or unipolar electrodes 40, 42 (also referred to as RV electrodes) are located proximate to a distal end of the lead 18. Referring briefly to FIGS. 3-3A, the electrodes 44, 45, 46 are located proximate to a distal end of the lead 20 and the bipolar or unipolar electrodes 56, 50 (FIG. 2) are located proximate to a distal end of the lead 22. Electrodes 44, 45, 46 and 47 can be bipolar electrodes, unipolar electrodes or a combination of bipolar and unipolar electrodes. Additionally, electrodes 44, 45, 46 and 47 have an electrode surface area of about 5.3 mm$^2$ to about 5.8 mm$^2$. Electrodes 44, 45, 46, and 47 are also referred to as LV1 (electrode 1), LV2 (electrode 2), LV3 (electrode 3), and LV4 (electrode 4), respectively. As shown, lead 20 includes a proximal end 92 and a distal end 94. The distal end 94 is placed in or near LV tissue. Skilled artisans appreciate that LV electrodes (i.e. left ventricle electrode 1 (LV1) 44, left ventricle electrode 2 (LV2) 45, left ventricle electrode 3 (LV3) 46, and left ventricle 4 (LV4) 47 etc.) on lead 20 can be spaced apart at variable distances. For example, electrode 44 is a distance 96a (e.g. about 21 mm) away from electrode 45, electrodes 45 and 46 are spaced a distance 96b (e.g. about 1.3 mm to about 1.5 mm) away from each other, and electrodes 46 and 47 are spaced a distance 96c (e.g. 20 mm to about 21 mm) away from each other.

The electrodes 40, 44, 45, 46, 47, 48 may take the form of ring electrodes, and the electrodes 42, 47, 50 may take the form of extendable helix tip electrodes mounted retractably within the insulative electrode heads 52, 54, 56, respectively. Each of the electrodes 40, 42, 44, 45, 46, 47, 48, 50 may be electrically coupled to a respective one of the conductors (e.g., coiled and/or straight) within the lead body of its associated lead 18, 20, 22, and thereby coupled to respective ones of the electrical contacts on the proximal end of the leads 18, 20, 22. The electrodes 40, 42, 44, 45, 46, 47, 48, 50 may further be used to sense electrical signals attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 45, 46, 47, 48, 50 to cause depolarization of cardiac tissue of the patient's heart 12. In some examples, as illustrated in FIG. 2, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 45, 46, 47, 48 and 50 may be used for unipolar sensing or pacing in combination with housing electrode 58. Further, any of electrodes 40, 42, 44, 45, 46, 47, 48, 50, 58, which are not being used to deliver pacing therapy, may be used to sense electrical activity during pacing therapy (e.g., for use in determining electrical activation times). Electrical activation time can be used to determine whether pacing (e.g. LV only pacing or biventricular pacing) produces effective contraction of the heart based on metrics of electrical dyssynchrony derived from the ventricular activation times.

Electrical activation time or local electrical activity is determined relative to timing of a fiducial, an indicator of a global cardiac event (e.g. timing of contraction of a chamber of the heart, timing of pacing of a chamber of the heart, etc.) For example, the fiducial may be the onset of QRS, the peak of QRS (e.g. minimum values, minimum slopes, maximum slopes), zero crossings, threshold crossings, etc. of a near or far-field EGM), onset of application of a pacing electrical stimulus, or the like. After a fiducial point is selected, activation times are determined by measuring time between the delivery of pacing stimulus using a pacing electrode and the appropriate fiducial point with the electrical activity sensed by a non-pacing electrode. The timing may be the initiation of the pacing signal or the like. The device delivering the pacing signal may include appropriate electronics to track and mark the timing of the pacing signal, which marked or tracked time may be used for purposes of determining local activation time and electrical dispersion as discussed above. The device that delivers the pacing signal may be a device configured for delivering CRT.

As described in further detail with reference to FIG. 4, the housing 60 may enclose a therapy delivery module that may include a stimulation generator for generating cardiac pacing pulses and defibrillation or cardioversion shocks, as well as a sensing module for monitoring the patient's heart rhythm. Cardiac pacing involves delivering electrical pacing pulses to the patient's heart, e.g., to maintain the patient's heart beat (e.g., to regulate a patient's heart beat, to improve and/or maintain a patient's hemodynamic efficiency, etc.). Cardiac pacing involves delivering electrical pacing pulses ranging from about 0.25 volts to about 8 volts and more preferably, between 2-3 volts.

The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity during pacing therapy (e.g., for use in determining activation times). In at least one embodiment, the LV elongated electrode 64 may be used to sense electrical activity of a patient's heart during the delivery of pacing therapy. Electrodes used to sense a response from cardiac tissue are transmitted to an ND converter to convert the analog signal to a digital signal. The digital signal is then transmitted to the microprocessor 80. The microprocessor 80 determines the level of response sensed at a particular electrode.

The configuration of the exemplary therapy system 10 illustrated in FIGS. 1-2 is merely one example. In other examples, the therapy system may include epicardial leads and/or patch electrodes instead of or in addition to the transvenous leads 18, 20, 22 illustrated in FIG. 1. Further, in one or more embodiments, the IMD 16 need not be implanted within the patient 14. For example, the IMD 16 may deliver defibrillation shocks and other therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. Other examples of therapy systems may include three transvenous leads located as illustrated in FIGS. 1-3. Still further, other therapy systems may include a single lead that extends from the IMD 16 into the right atrium 26 or the right ventricle 28, or two leads that extend into a respective one of the right atrium 26 and the right ventricle 28.

Figure 4:
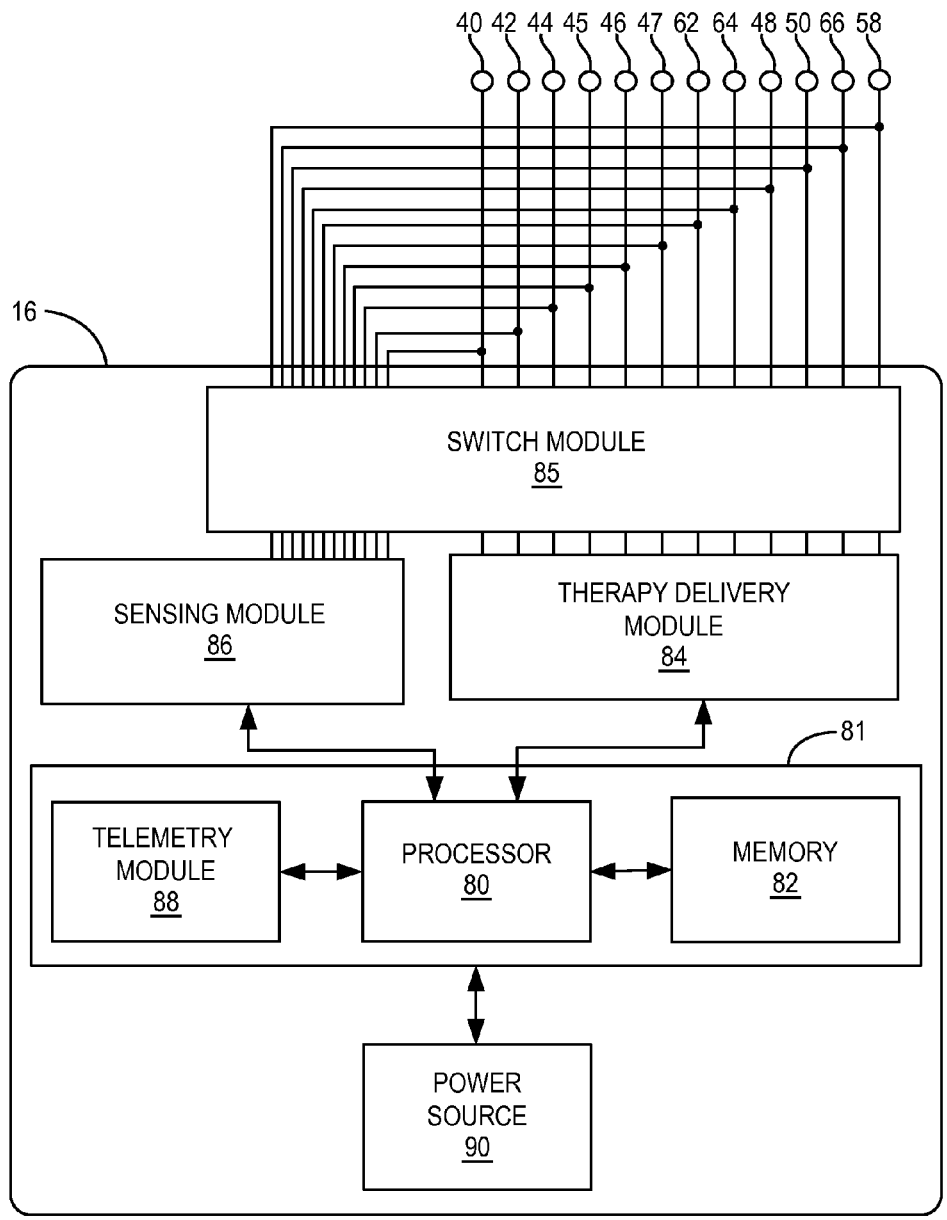
FIG. 4 is a block diagram of an exemplary IMD, e.g., the IMD of FIGS. 1-2.

FIG. 4 is a functional block diagram of one exemplary configuration of the IMD 16. As shown, the IMD 16 may include a control module 81, a therapy delivery module 84 (e.g., which may include a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random access memory (RAM), read-only memory (ROM), non-volatile RAM (NVRAM), electrically-erasable programmable ROM (EEPROM), flash memory, and/or any other digital media.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control the therapy delivery module 84 to deliver electrical stimulus such as, e.g., pacing pulses with the amplitudes, pulse widths, frequency, or electrode polarities specified by the selected one or more therapy programs (e.g., pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 45, 46, 47, 48, 50, 58, 62, 64, 66.

For example, therapy delivery module 84 may deliver pacing stimulus (e.g., pacing pulses) via ring electrodes 40, 44, 48 coupled to leads 18, 20, and 22, respectively, and/or helical tip electrodes 42, 46, and 50 of leads 18, 20, and 22, respectively. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy to a pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 45, 46, 47, 48, 50, 58, 62, 64, 66 to monitor electrical activity of the heart 12, e.g., electrocardiogram (ECG)/electrogram (EGM) signals, etc. The ECG/EGM signals may be used to monitor heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may also be used with the sensing module 86 to select which of the available electrodes are used, e.g. to sense electrical activity of the patient's heart. In some examples, the control module 81 may select the electrodes that function as sensing electrodes via the switch module within the sensing module 86, e.g., by providing signals via a data/address bus. In some examples, the sensing module 86 may include one or more sensing channels, each of which may include an amplifier.

In some examples, sensing module 86 includes a channel that includes an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter (ND) for storage in memory 82 as an electrogram (EGM). In some examples, the storage of such EGMs in memory 82 may be under the control of a direct memory access circuit. The control module 81 (e.g., using the processor 80) may employ digital signal analysis techniques to characterize the digitized signals stored in memory 82 to detect and classify the patient's heart rhythm from the electrical signals. For example, the processor 80 may be configured to measure activation times of cardiac tissue using EGMs from one or more electrodes in contact, or in proximity, with cardiac tissue by employing any of the numerous signal processing methodologies known in the art.

If IMD 16 is configured to generate and deliver pacing pulses to the heart 12, the control module 81 may include a pacer timing and control module, which may be embodied as hardware, firmware, software, or any combination thereof. The pacer timing and control module may include one or more dedicated hardware circuits, such as an ASIC, separate from the processor 80, such as a microprocessor, and/or a software module executed by a component of processor 80, which may be a microprocessor or ASIC. The pacer timing and control module may include programmable counters which control the basic time intervals associated with DDD, WI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

Intervals defined by the pacer timing and control module within control module 81 may include atrial and ventricular pacing escape intervals, refractory periods during which sensed P-waves and R-waves are ineffective to restart timing of the escape intervals, and/or the pulse widths of the pacing pulses. As another example, the pacer timing and control module may define a blanking period, and provide signals from sensing module 86 to blank one or more channels, e.g., amplifiers, for a period during and after delivery of electrical stimulation to the heart 12. The durations of these intervals may be determined in response to stored data in memory 82. The pacer timing and control module of the control module 81 may also determine the amplitude of the cardiac pacing pulses.

During pacing, escape interval counters within the pacer timing/control module may be reset upon sensing of R-waves and P-waves. Therapy delivery module 84 (e.g., including a stimulation generator) may include one or more pacing output circuits that are coupled, e.g., selectively by the switch module 85, to any combination of electrodes 40, 42, 44, 45, 46, 47, 48, 50, 58, 62, or 66 appropriate for delivery of a bipolar or unipolar pacing pulse to one of the chambers of heart 12. The control module 81 may reset the escape interval counters upon the generation of pacing pulses by therapy delivery module 84, and thereby control the basic timing of cardiac pacing functions, including anti-tachyarrhythmia pacing.

In some examples, the control module 81 may operate as an interrupt driven device, and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as the programmer 24 as described herein with respect to FIG. 1. For example, under the control of the processor 80, the telemetry module 88 may receive downlink telemetry from and send uplink telemetry to the programmer 24 with the aid of an antenna, which may be internal and/or external. The processor 80 may provide the data to be uplinked to the programmer 24 and the control signals for the telemetry circuit within the telemetry module 88, e.g., via an address/data bus. In some examples, the telemetry module 88 may provide received data to the processor 80 via a multiplexer. In at least one embodiment, the telemetry module 88 may be configured to transmit an alarm, or alert, if the pacing therapy becomes ineffective or less effective.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

After the LV lead 20 has been properly positioned on or near the LV tissue, schematically shown in FIG. 3, a variety of pacing configurations (e.g. biventricular pacing configurations, LV only pacing etc.) can be tested. Data generated from each pacing configuration can be useful in determining the optimal LV electrode from which to pace the LV. Biventricular pacing configurations are defined by a RV electrode pacing the RV while one or more LV electrodes pace the LV. Each biventricular configuration employs a different LV electrode (e.g. LV1, LV2, LV3, and LV4 etc.) for pacing.

Exemplary methods and/or devices described herein evaluate the effectiveness of pacing based on metrics of electrical dyssynchrony derived from the measured cardiac electrical activation times for each biventricular pacing configuration employing a different LV electrode. FIGS. 5-8 flow diagrams present different exemplary methods for selecting an optimal LV electrode.

Figure 5:
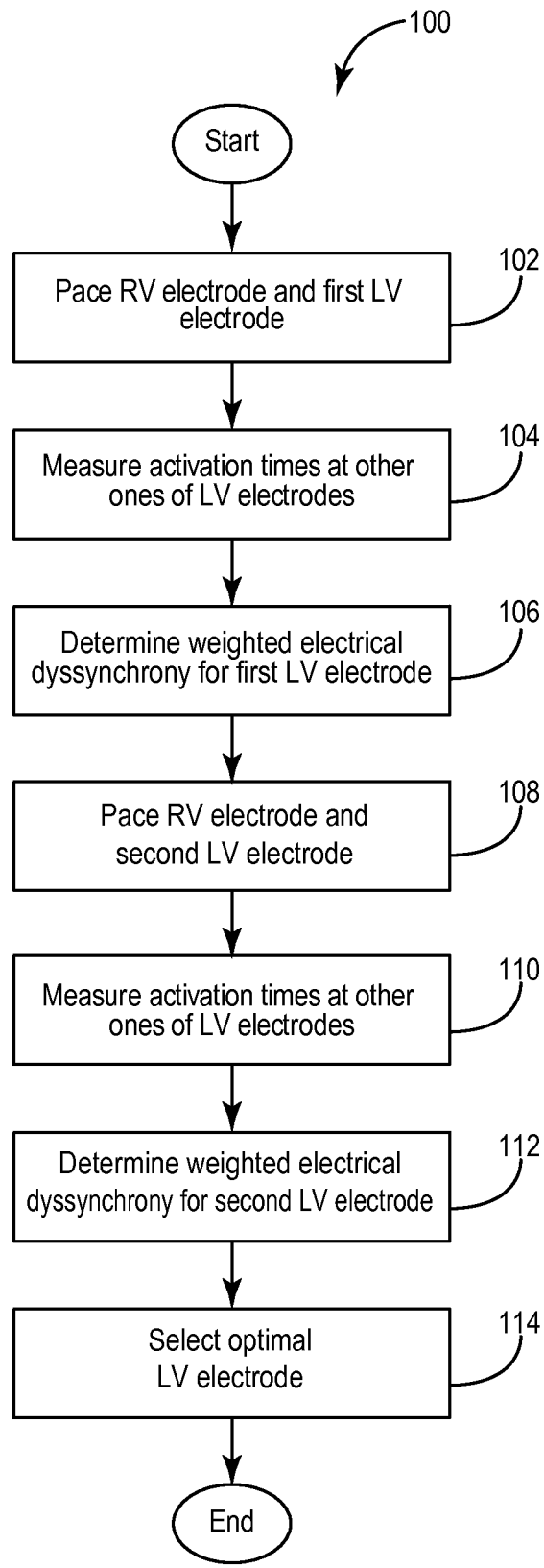
FIG. 5 is a general flow chart of an exemplary method that involves determining a weighted electrical dyssynchrony without a baseline for selecting an optimal left ventricle electrode to pace a left ventricle.

Exemplary method 100, depicted in FIG. 5, evaluates different biventricular pacing configurations in order to determine which LV electrode on lead 20 is optimal for pacing the LV. Each of the available biventricular pacing configurations is serially tested and evaluated by programmer 24 as to its effectiveness based on the metrics of electrical dyssynchrony. The optimal biventricular pacing configuration is selected based on one or more of these metrics.

At block 102, the programmer 24 switches the RV electrode 42 and one of the LV electrodes 44, 45, 46, 47 to a pacing mode while the other LV electrodes remain in the sensing mode. The LV electrode that is selected for pacing the LV is designated as the j-th LV electrode. The first LV electrode out of the plurality of LV electrodes to pace the LV is referred to in the claims as the first LV electrode. The programmer 24 includes a pulse generator that generates pacing pulses (e.g. 2-3 volts amplitude) that are delivered through the pacing LV electrode to the LV while other pacing pulses (e.g. 2-3 volts amplitude) are transmitted through the RV electrode to the RV. The non-pacing LV electrodes sense from the LV tissue the electrical response such as the activation times. The sensed signals are transmitted to an A/D converter that converts the analog signals to digital signals. Digital signals are then transmitted to the microprocessor 80 so that sensed signals can be measured and then stored into memory 82 at operation 104.

At block 106, after obtaining the electrical activation times (e.g. determined with respect to the timing of the earliest ventricular pacing or any other suitable means) at non-pacing electrodes, the microprocessor 80 determines the weighted electrical dyssynchrony index for the first biventricular pacing configuration. Electrical dyssynchony or cardiac dyssynchrony involves improperly timed electrical activation of one or more different parts of the heart.

An electrical dyssynchrony index (ED) of LV electrical dyssynchrony [ED(j, A, D)] can be computed for each pacing electrode j from a linear combination of electrical activation times (AT(i, A, D)) at each sensing LV electrode denoted by i. "A" of ED(j, A, D) refers to the atrio-ventricular delay between atrial sense (pace) and the first ventricular pacing pulse, and "D" refers to the time delay between the pacing pulses in the RV and the LV. A determination of ED for each LV electrode may be made initially at a nominal values of A and D. A nominal value of "A" may be 50 ms, the nominal value of D can be about 0 ms, which is simultaneous biventricular pacing.

ED is determined by a weighted linear combination of electrical activation times in which individual weights are determined depending upon the lead-geometry and the inter-electrode spacing on the lead. In particular, ED is weighted by a suitable factor w(i, j) that is based on the distance of the sensing electrode (designated "i", from the pacing electrode (designated "j"). Accordingly, the equation for calculating a weighted ED is as follows:

$$ED(j,A,D)=\Sigma_{i=1}^{n} w(i,j) AT(i,A,D)$$

"n" is the total number of LV electrodes.

Only valid ED are used to determine an optimal LV electrode from which to pace. A valid ED typically occurs over multiple beats (e.g. 5 beats etc.) during pacing from a selected LV electrode to ensure that measurements are consistent and repeatable. Additionally, automatic LV and RV capture detection is turned on to ensure that pacing pulse delivered in each ventricle captures. ED is not computed for instances where RV or LV or both RV and LV do not capture. Capture detection can be verified by determining the amplitude of an evoked response at the pacing electrode. For example, an amplitude greater than 0.5 mV may be indicative of capture. Variability of ED values should be less than a certain predetermined value such as 5 ms. Additionally, valid ED requires AT(i, A, D)>0 for all i where i designates the LV electrode number. Negative values for one or more AT(i) are omitted. A negative value of AT(i, A,D) may be caused by anomalous ventricular activation such as a premature beat. If |AT(i+1, A, D)−AT(i, A, D)|>50 ms, then slow electrical conduction can exist or a block, attributable to infarct or functional block, can be identified between electrodes i and i+1.

ED is typically computed with interventricular (V-V) delay (D) value and/or the atrioventricular delay (A) set at a constant value when evaluating each LV electrode. For example, the A-V delay can be set at a preselected value (e.g. 0 to about 50 ms etc.) while the V-V delay can also be preselected (e.g. 0 to 55 ms) for each biventricular pacing configuration such as LV1+RV, LV2+RV, LV3+RV, LV4+RV . . . LVN+RV where N is the total number of electrodes. Assume A=50 ms and D=0 (i.e. simultaneous biventricular pacing) while evaluating each of the LV electrodes or with a V-V delay as is discussed in greater detail below. Additionally, skilled artisans appreciate that the activation time for the pacing electrode which captures the tissue may be 0 or may be skipped.

After an ED has been determined for the first LV electrode, the programmer 24 automatically selects, a second biventricular pacing configuration in which a second LV electrode paces the LV while the RV electrode paces the RV at operation 108. The first LV electrode is switched to the sensing mode. The programmer 24 causes the pulse generator to generate pacing pulses (e.g. 2-3 volts amplitude) that are delivered through the second LV electrode to the LV while other pacing pulses (e.g. 2-3 volts amplitude) are transmitted through the RV electrode to the RV. The non-pacing LV electrodes sense the electrical response (e.g. activation time data etc.) from the LV tissue. The sensed signals are transmitted to an A/D converter that converts the analog signals to digital signals. Digital signals are then transmitted to the microprocessor 80 so that sensed signals can be measured and then stored into memory 82 at operation 110. After obtaining the electrical activation times at non-pacing electrodes, the microprocessor 80 determines a weighted electrical dyssynchrony index associated with the second LV pacing electrode at operation 112. Skilled artisans appreciate that blocks 108-112 are repeated for all of the remaining LV electrodes (e.g. LV3, LV4 etc.) at the distal end of lead 20.

Once two or more valid EDs have been calculated, electrode elimination rules can be applied to the EDs to eliminate LV electrodes in order to determine the optimal LV electrode at operation 114. The ED for each electrode can be determined for the set of electrodes before application of the set of rules. Alternatively, the rules can be applied after determining an ED for any two electrodes and once one of the two electrodes is eliminated, an ED is calculated for yet another electrode to be compared to the ED of the remaining electrode.

Examples of the manner in which ED are calculated are presented below as to the set of LV electrodes (i.e. left ventricle electrode 1 (LV1) 44, left ventricle electrode 2 (LV2) 45, left ventricle electrode 3 (LV3) 46, and left ventricle 4 (LV4) 47 etc.) shown on the LV medical electrical lead 20; however, it is appreciated that teachings presented herein can be applied to two or more LV electrodes on a medical electrical lead.

While pacing from LV1 during simultaneous biventricular pacing (D=0) and A=50 ms, the ED is computed below. For these nominal values of A and D, the ED for the biventricular pacing with the j-th LV electrode and the activation time at the i-th LV electrode during such biventricular pacing are represented by ED(j) and AT(i) respectively. The weighted ED for pacing at LV1 can be rewritten as follows:

$$ED(1)=AT(1)+AT(2,3)+AT(4)/2 \text{ where } AT(2,3)=[AT(2)+AT(3)]/2$$

Since LV2 and LV3 are substantially close, the AT of LV2 and LV3 are averaged together. The AT associated with LV4 is muliplied by a constant number w(i, j). W(i, j) is a weighting factor that depends on the distance from LV1 to LV4 as compared to the distance between LV electrodes (2,3) and LV1. In this example, w(4,1) is ½ since the distance from LV1 to LV4 is twice as long as the distance from electrodes (2,3) to LV1. W(i, j) can be adjusted depending upon the LV medical electrical lead and the spacing used between the plurality of electrodes thereon.

Evaluation of ED and activation propagation is also performed while pacing from other LV electrodes 2, 3 and 4 in the quadripolar lead 20 during simultaneous biventricular pacing. The equation for calculating weighted ED at LV2 or LV3 is as follows:

$$ED(2)=AT(1)+AT(2,3)+AT(4)$$

$$ED(3)=AT(1)+AT(2,3)+AT(4) \text{ where } AT(2,3)=[AT(2)+AT(3)]/2$$

Since the spacing between LV2 and LV3 is less than 2 mm, and LV1 and LV4 are about equidistant from LV2 and LV3, the activation times are weighted equally while computing ED for LV2 and LV3.

The equation for calculating a weighted ED at LV4 is as follows:

$$ED(4)=AT(1)/2+AT(2,3)+AT(4) \text{ where } AT(2,3)=[AT(2)+AT(3)]/2$$

After weighted ED calculations are performed, the optimal LV electrode is selected at block 114.

Figure 6A:
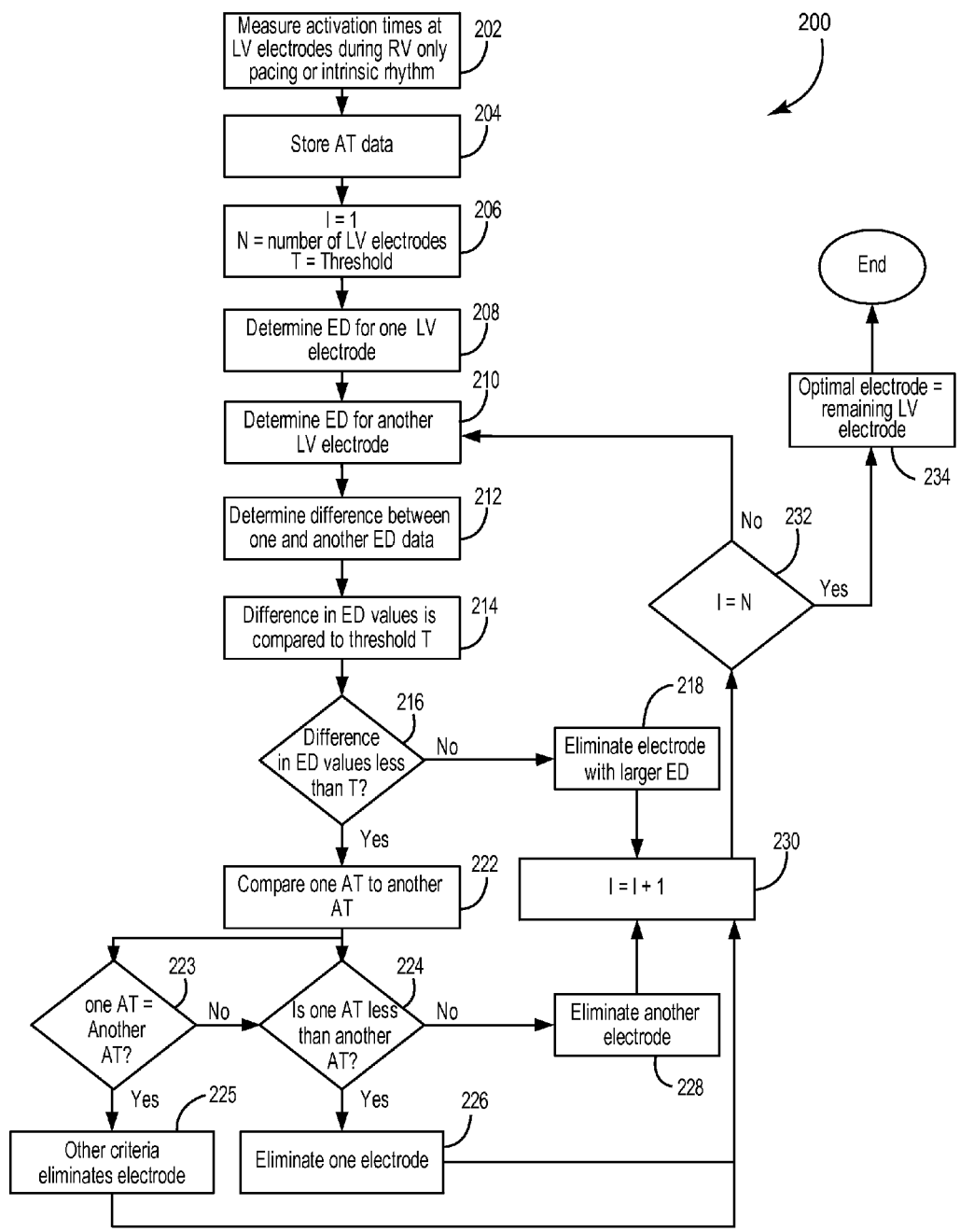
FIG. 6A is a general flow chart of an exemplary method that involves selecting an optimal left ventricle electrode to pace a left ventricle.

FIG. 6A shows a method 200 in which the optimal LV electrode is selected from the plurality LV electrodes (e.g. LV1, LV2, LV3, and LV4) through a process of electrode elimination. The process of elimination employs two different types of electrode comparisons that are used to eliminate an electrode from each pair of electrodes until the sole remaining electrode is deemed to be the optimal LV electrode. The process of eliminating an electrode begins at block 202 in which activation times are measured at the LV electrodes (e.g. LV1, LV2, LV3, and LV4) during baseline rhythm which may constitute RV only pacing or intrinsic rhythm. RV only pacing occurs when the pulse generator from the programmer 24 delivers electrical stimulation (i.e. pacing pulses) through an RV electrode to the RV and none of the LV electrodes are used to pace the LV. Sensing the activation times at all of the LV electrodes (e.g. LV1, LV2, LV3, and LV4) during RV only pacing or during intrinsic rhythm can be performed any time after LV lead 20 has been placed near and/or on LV tissue. For example, RV only pacing can occur before or after any of the biventricular pacing configurations are tested.

At block 204, the activation times associated with each of the LV electrodes are stored into the memory 82. At block 206, variables threshold (T) level, integer (I), and total number of electrodes (N) (e.g. N=4 on the distal end of lead 20) are initialized, set, and stored into memory 82. Threshold T can be predetermined and input into the programmer 24 by the user before evaluating each LV electrode (e.g. LV1, LV2, LV3, LV4). Preferably, T equals 15 ms or less. A value of T equal to 15 ms or less can be typical of a left bundle branch block (LBBB) patient with a QRS of 150 ms. Additionally, T equal to 15 ms or less is typically about a 10% time of total ventricular activation. In one or more other embodiments, T equals 10 ms or less.

I and N are used in a counting loop (i.e. blocks 206, 230 and 232) that ensures that data for each LV electrode (e.g. LV1, LV2, LV3, and LV4) are analyzed before the optimal LV electrode is selected. I=1 since ED is determined for only one LV electrode at block 208 by processor 80 and stored in memory 82. The data for determining the ED for one LV electrode can be selected from any one of the LV electrodes (e.g. LV1, LV2, LV3, and LV4). At block 210, data for another LV electrode is retrieved from memory 82 by processor 80. Determining the ED for another LV electrode means any other LV electrode data not previously analyzed. For example, if the ED for one LV electrode at block 208 is data related to LV1, then data for another LV electrode can be related to LV2, LV3, or LV4. For the sake of illustration, assume that the data for another LV electrode is associated with LV2. Therefore, the ED for LV2 is calculated by processor 80 and stored in memory 82.

At block 212, the difference in magnitude between one ED data and another ED data is determined. For example, the ED data for one electrode (i.e. LV2) is subtracted from ED data for another electrode (i.e. LV1). At block 214, the difference between one ED data (i.e. ED1) and another ED data (i.e. ED2) is compared to a threshold level T (also referred to as delta T or ΔT). At block 216, if the difference is not less than T, then the NO path can be followed to block 218. At operation 218, whichever electrode is associated with a larger ED is automatically eliminated from consideration as a potential optimal LV electrode irrespective of the eliminated electrode's activation time obtained during intrinsic rhythm or RV only pacing.

The counting loop increases the variable I by one at block 230. At block 232, a determination is made as to whether I=N. Since after the first pass of the counting loop I=2 and N=4, the NO path transfers control to block 210 to retrieve ED data for yet another LV electrode. ED is then calculated for yet another LV electrode (e.g. LV3) and then stored into memory 82. Skilled artisans appreciate that after an electrode is eliminated, at either block 218 or 228, and ED data for another electrode is retrieved, a swapping operation may be performed. For example, if data for LV2 is initially designated as "another LV electrode" and LV2 is eliminated, then data for LV3 is swapped for the ED data for LV2 and the ED data for LV3 is now stored in the register for "another ED data" at block 210. The electrode pair comparisons are then between LV1 and LV3 and so on.

Returning to block 216, if the difference in ED value is less than T, the YES path transfers control to block 222. At block 222, the baseline (intrinsic rhythm or RV only pacing) AT data for one electrode (i.e. LV1) is compared to the baseline AT data for another electrode (i.e. LV3). The baseline AT data is preferably obtained during intrinsic rhythm or RV only pacing. Comparing one baseline AT to another baseline AT can involve a sorting function that places the data in ascending order or descending order. At block 224, a determination is made as to whether one baseline AT is less than another baseline AT. If one baseline AT is less than another baseline AT, the YES path can be followed to block 226.

Returning to block 223, if one baseline AT is equal to the other baseline AT, then both electrodes are retained in a preference list. At block 225, one of the two electrodes can be eliminated based upon additional or other criteria such as lower capture threshold, higher impedance (i.e., reduced energy required to pace), or absence of phrenic stimulation could be considered (by the user) to select the best electrode of two electrodes that have equivalent ATs.

At block 226, one electrode (i.e. LV1) is eliminated. I is incremented by 1 at block 230. At block 232, a determination is made as to whether I=N, which essentially determines whether ED data has yet to be retrieved.

Returning to block 224, if one baseline AT is not less than another baseline AT, the NO path can be followed to block 228 in which another electrode (i.e. LV2) is eliminated. The counting loop at block 232 is then used to determine whether any additional ED data must be processed. At block 232, once I=N, no additional ED data needs to be processed. Therefore, the YES path can be followed to block 234. The optimal electrode is then designated as the LV electrode that remains or has not been eliminated. The optimal LV electrode is set to pace the LV automatically by programmer 24 or manually by the user.

Examples, presented below, show the electrode elimination process used to select an optimal LV electrode. In these examples, assumptions are made. For blocks 222, and 224, activation times for the LV electrodes are performed during RV only pacing or during intrinsic rhythm. In contrast, the ED data was generated using the biventricular pacing configurations, as previously described herein. Additionally, a quadripolar LV lead 20 is used that includes four LV electrodes, LV1, LV2, LV3, and LV4; however, skilled artisans appreciate that other embodiments could use two or more LV electrodes on a lead 20 such as two or more electrodes on one lead and two or more electrodes on another lead. Each example will be described relative to FIG. 6A.

In the first example, assume that the order of activation times during RV only pacing or intrinsic rhythm is AT(LV4)>AT(LV1)>AT(LV2)>AT(LV3) with LV4 being the latest activation time and LV3 being the earliest activation time. Assume also that the values of ED, determined from the biventricular configurations previously discussed are as follows: ED(1)=50 ms, ED(2)=55 ms, ED(3)=58 ms, and ED(4)= 74 ms. Other assumptions include that D=0, A is a constant (e.g., 50 ms), and that a predetermined threshold T of 15 ms is used to analyze the ED data. Processor 80 retrieves ED data such as ED(1) and ED(2) at blocks 208, 210, respectively.

At block 212, the difference in magnitude between ED(1) and ED(2) is calculated as follows:

ED(2)−ED(1)=55 ms−50 ms=5 ms

At block 214, the difference in ED(1) and ED(2) is compared to the threshold T. At block 216, a determination is made as to whether the difference in ED(1) and ED(2) is less than the predetermined threshold of 15 ms. Since the difference (i.e. 5 ms) in ED(1) and ED(2) is less than T, the YES path is followed to block 222 in which the AT values (i.e. AT(1), AT(2)) are compared. In one or more embodiments, the compare function can also include sorting the activation times in ascending order or descending order.

At block 223, if one baseline AT is equal to the other baseline AT, then both electrodes are retained in a preference list. One of the two electrodes is eliminated based upon the previously described criteria at block 225. If one AT does not equal another AT, the NO path goes to block 224.

At block 224, a determination is made as to whether one AT (i.e. AT1) is less than another AT (i.e. AT2). As is known from the given facts, the activation time for one AT (i.e. AT1) is greater than another AT (i.e. AT2). The NO path can be followed to block 228, which causes the elimination of another electrode (i.e. LV2). The variable I is increased by 1 at block 230. At block 232, a determination is made as to whether I=N. Since I=2 and N=4, I does not equal N. The NO path returns to block 210 for processor 80 to retrieve from memory 82 another ED value for another LV electrode (e.g. LV3).

The ED value of LV3 is then subtracted from the ED value for LV1 at block 212.

ED(3)−ED(1)=58 ms−50 ms=8 ms

The difference in magnitude (i.e. 8 ms) between ED(1) and ED(3) is less than the predetermined threshold of 15 ms at block 216. The YES path can be followed to block 222. At block 222, the activation times between AT(1) and AT(3) are compared to each other. As previously stated, AT(1) is greater than AT(3). LV3 is then eliminated based on its earlier activation time compared to LV1 at block 228.

At block 230, the variable I is again increased by 1 which causes I=3. A determination is made as to whether I=N at block 232. Since I does not equal N, the NO path is followed to block 210. The ED data for the next electrode, ED(4), is then then retrieved at block 210.

ED(1) data, associated with LV1, is subtracted from ED(4) at block 212. At block 214, the difference in ED values is 24 ms, which is greater than the pre-determined threshold of 15 ms. The NO path can be followed to block 218 in which the electrode to be eliminated is associated with the larger ED data. The electrode with the larger ED, i.e. LV4, is eliminated without any comparison being performed between the activation times of LV1 and LV4.

At block 230, I is again incremented by 1 causing I=4. At block 232, a determination is made as to whether I=N. Since I=4 and N=4, then I=N. The YES path can be followed to block 234, which designates the optimal electrode is LV1 since LV1 is the last remaining electrode that was not eliminated in the exhaustive electrode-pair comparisons. LV1 is then selected as the final electrode for delivering CRT.

A second example shows how the selection is made when ED values of all electrodes are almost equivalent or similar. For example, assume the order of activation times during intrinsic rhythm (or RV only pacing) are such that AT(LV4)>AT(LV1)>AT(LV2)>AT(LV3). LV4 is associated with the latest activation time and LV3 is associated with the earliest activation time. From the biventricular pacing configurations, the ED values were determined such that ED(1)=30 ms, ED(2)=33 ms, ED(3)=25 ms, and ED(4)=28 ms. Referring to FIG. 6, ED data is retrieved for one LV electrode such as ED(1) at block 208. At block 210, ED data is retrieved for another LV electrode such as ED(2) at block 212. At block 212, the difference in ED values is calculated follows:

ED(2)−ED(1)=33 ms−30 ms=3 ms

At block 214, the difference in ED(1) and ED(2) is compared to predetermined threshold of 15 ms. As shown above, the difference in ED(1) and ED(2) is only 3 ms which is less than the predetermined threshold of 15 ms. At block 216, a determination is made as to whether the difference in ED values is less than the threshold. Since the difference is 3 ms is less than 15 ms, the YES path can be followed to block 222 in which one AT (i.e. AT(1)) is compared to another AT (i.e. AT(2)). From the comparison, it was determined that AT(1) is greater than AT(2). At block 224, a NO path can be followed to block 228 that eliminates another electrode (i.e. LV2). At block 230, I is incremented by I causing I=2. At block 232, a determination is made as to whether I=N. Since I=2 and N=4, I does not equal N. Therefore, the NO path returns to block 210 in which another ED data (i.e. ED3) is retrieved from memory 82.

At block 212, the difference between ED(1) and ED(3) is calculated as follows:

ED(1)−ED(3)=30 ms−25 ms=5 ms

The difference in ED values of LV1 and LV3 is 5 ms which is less than the threshold value of 15 ms at block 216. The YES path can be followed to block 222 which compares AT(1) to AT(3). Since AT(3) is greater than AT(1), the electrode LV3 is eliminated at block 228 based on its earlier activation time compared to the electrode LV1. Again, I is incremented by 1 at block 230 and another determination is made as to whether I=N at block 232. Since I=3, I does not equal N. Therefore, another ED data such as ED(4) is retrieved from memory 82.

LV4 can then be compared with the electrode LV1. The difference in ED values of electrode LV1 and the electrode LV4 is 2 ms. At block 224, one AT is found to be less than another AT. The electrode LV1 is eliminated due to AT(LV1) having an earlier activation time compared to AT(4). Again, I is incremented by 1 causing I=4. Since I=N at block 232, the optimal electrode is LV4. LV4 is chosen as the final or optimal electrode from which to pace the LV since LV4 was not eliminated.

A third example is presented in which activation times during RV only pacing or intrinsic rhythm of the four electrodes are such that AT(LV4)>AT(LV1)>AT(LV2)>AT(LV3). Additionally, the ED values generated from the biventricular pacing configurations are ED(1)=60 ms, ED(2)=40 ms, ED(3)=38 ms, and ED(4)=62 ms. Referring to FIG. 6, processor 80 retrieves ED(1) data and ED(2) data from memory 82 at blocks 208, 210, respectively. At block 212, the difference in ED values can be calculated by the following:

ED(1)−ED(2)=60 ms−40 ms=20 ms

At block 216, since the difference in ED values associated with LV1 and LV2 is 20 ms which exceeds the threshold of 15 ms, the NO path can be followed to block 218 in which the electrode with the higher ED value, i.e. electrode LV1 is eliminated. I is incremented by 1 at block 230. A determination is then made as to whether I=N at block 232. Since I=2, and N equals 4, the NO path returns to block 210 to retrieve ED(3) data.

At block 212, the difference in ED values can be calculated as follows:

ED(3)−ED(2)=38 ms−40 ms=−2 ms

Since the difference in magnitude between ED(2) and ED(3) is 2 ms, which is less than the threshold of 15 ms, the YES path can be followed to block 222. At block 222, one AT (i.e. LV3) is compared to another AT (i.e. LV2). LV3 is associated with a AT that is less than the AT for LV2. At block 224, a determination is made as to whether one AT (i.e. LV3) is less than another AT (i.e. LV2). At block 226, electrode LV3 is eliminated.

Again, I is incremented by 1 at block 230. Therefore, I=3. At block 232, I does not equal N since I=3 and N=4; therefore, at block 210, ED(4) is retrieved from memory 82.

At block 212, the difference between ED(4) and ED(2) can be shown as follows:

ED(4)−ED(2)=62 ms−40 ms=22 ms

Since the difference in their ED values is 22 ms, well above the threshold of 15 ms, the NO path can be followed to block 218. At block 218, the electrode associated with the larger ED value is eliminated. Since ED(4) is larger (i.e. 62 ms) than ED(2) (i.e. 40 ms), LV4 is eliminated. I is again incremented by 1 at block 230 thereby causing I to be equal to 4. At block 232, I=N; therefore, the YES path can be followed to block 234. The optimal electrode is LV2. LV2 is then used to pace the LV.

Figure 6B:
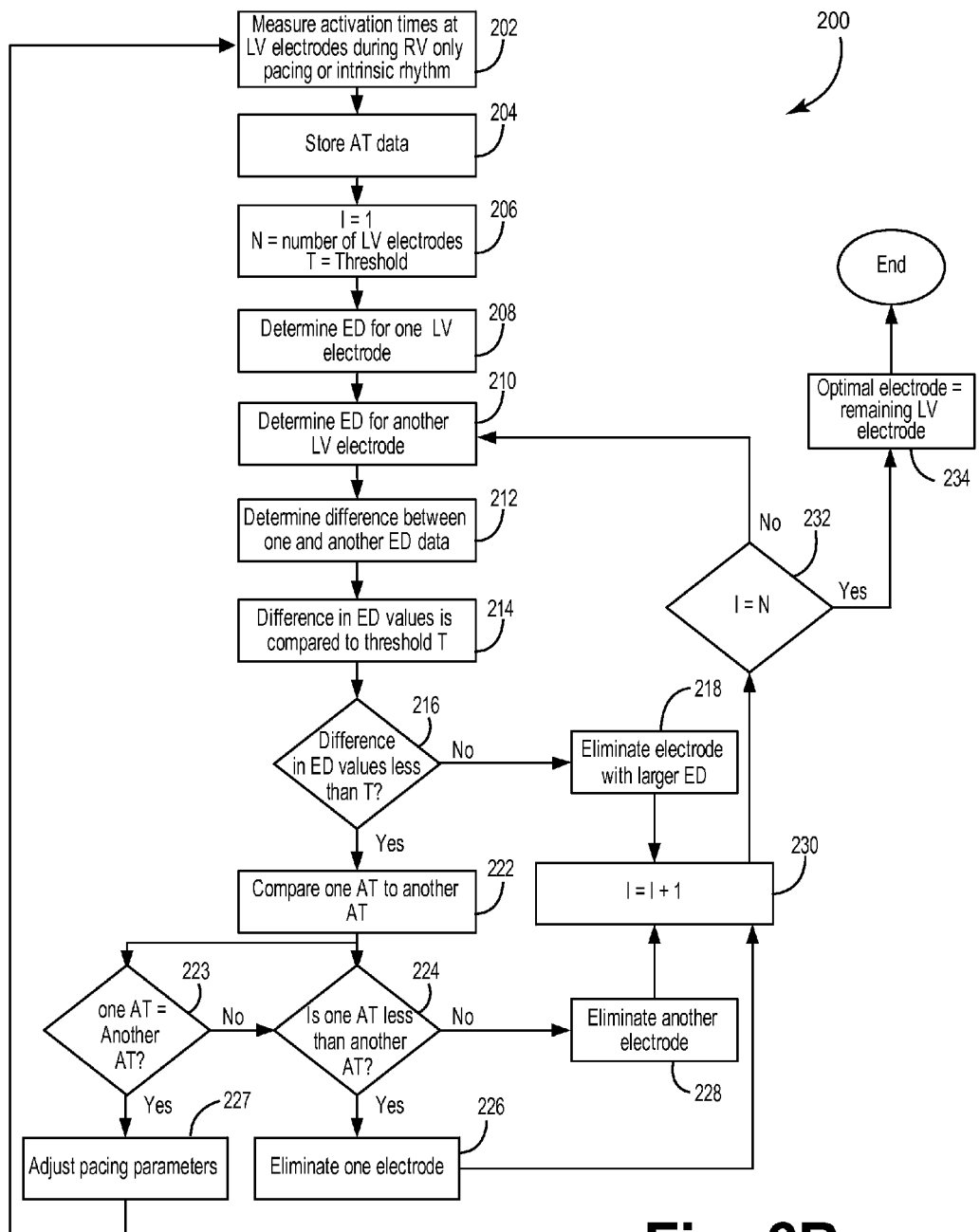
FIG. 6B is a general flow chart of another exemplary method that involves selecting an optimal left ventricle electrode to pace a left ventricle.

The method embodied in FIG. 6B is the same as FIG. 6A except block 225 is replaced by block 227. As previously described relative to block 223, if one baseline AT is equal to the other baseline AT, then both electrodes are retained in a preference list. One of the two electrodes can be eliminated based upon additional or other criteria. For example, the pacing pulse can be automatically adjusted (e.g. increased or decreased) at block 227. Equivalent electrodes are re-evaluated under method 200 by returning to block 202 using the new pacing criteria to determine whether a difference exists between the two electrodes. For example, the pacing pulse can be increased by 0.25 volts, 0.5 volts, 0.75 volts and so on. After rechecking the electrodes under method 200 using the increased pacing pulse, more than likely, a difference will exist between the two electrodes and the electrode that under performs is eliminated. If not, the pacing criteria can again be modified and the electrodes rechecked under method 200. The pacing criteria can be continuously adjusted and the electrodes evaluated under method 200 until a difference exists between the electrodes and one of the electrodes can be eliminated. If one AT does not equal another AT, the NO path goes to block 224.

A set of LV electrode elimination rules can be summarized below which can be applied to scenarios in which an anatomic block is present or not present. An anatomic block is a difference between two AT that is greater than a threshold $T_{AT}$. One LV electrode elimination rule is that when all electrodes have equivalent ED values, the LV electrode with the latest activation during RV only pacing or intrinsic rhythm is selected for final CRT therapy. However, if one LV electrode is associated with a higher ED compared to another LV electrode (i.e. a difference exceeding the predetermined threshold), the electrode with the higher ED is eliminated as a possible choice, irrespective of the activation times during intrinsic rhythm or RV only pacing.

Five examples are presented below in order to illustrate application of rules for selecting an optimal LV electrode, including different scenarios from simple ones when the LV lead in an area of electrically normal tissue, to more complicated scenarios when the LV lead is across an area of anatomic block (for e.g. due to scar) or functional block. With respect to the five examples, assumptions were made. For example, lead 20 includes four LV electrodes such as LV1, LV2, LV3, and LV4. Additionally, the baseline activation times are determined during RV only pacing or through intrinsic rhythm. It is further assumed that the baseline activation times are ranked in the order such that LV1>LV2>LV3>LV4, wherein LV1 is associated with the latest activation time. Moreover, ED data is generated from biventricular pacing configurations. Pacing pulses for biventricular pacing configurations range from about 0.25 volts to about 8 volts and more preferably, are delivered at 2 to 3 volts amplitude for both RV and LV pacing.

A first example or baseline involves the use of the LV lead 20 in normally conducting tissue with no functional or anatomic block. The baseline example can be used for comparative purposes with the subsequent examples in which an anatomic block exists. Suppose the activation times during, for example, intrinsic rhythm are sensed at LV electrodes 1, 2, 3 and 4 are ranked in the order LV1>LV2>LV3>LV4, so that LV1 is the latest activation time.

After the activation times have been determined, the ED data can be generated for each biventricular pacing configuration. For example, a LV electrode such as LV1 is selected to pace the LV by processor 80. Pacing pulses at 2 to 3 volts are delivered through LV1 to the LV while the RV electrode simultaneously paces the RV.

The activation times for the LV electrodes are sensed in response to the biventricular pacing of the LV and RV. AT(1) is equal to zero since LV1 is used to pace the LV. The electrical ATs in the LV tissue are sensed and measured for each non-pacing LV electrode (e.g. LV2, LV3 and LV4). AT(2,3) was measured at 25 ms, while AT(4) was measured at 50 ms. The equation for calculating ED as to LV1 is as follows:

ED(1)=AT(1)+AT(2,3)+AT(4)/2=0+25+(50/2)=50 ms

LV2 was then selected and paced at 2 to 3 volts amplitude while the RV electrode paces (e.g. at 2 to 3 volts amplitude) the RV. Electrical activation times were measured at the non-pacing LV electrodes. AT(2,3) is equal to 0. AT(1) was measured at 25 ms, and AT(4) was measured at 25 ms. The equation for calculating ED as to LV2 or LV3 is as follows:

ED(2 or 3)=AT(1)+AT (2,3)+AT(4)=(25+0+25)ms=50 ms

LV4 was then paced while the RV electrode simultaneously delivered pacing pulses to the RV. AT(4) is equal to zero since LV4 is used to pace the LV. Electrical activation times were measured such that AT(1) equaled 50 ms, and AT(2,3) equaled 25 ms. The equation for calculating ED as to LV4 is as follows:

ED(4)=AT(1)/2+AT(2,3)+AT(4)=(25+25+0)ms=50 ms

Since all ED values associated with each LV electrode are similar (e.g. difference between one ED value and another ED value equal to or less than a predetermined threshold such as 15 ms), the optimal pacing site is located at the latest activation site in the LV during intrinsic rhythm or RV only pacing. Therefore, LV1 is the best or optimal LV electrode from which to pace the LV. Table 1 presented below summarizes the results.

Table 1 summarizes the biventricular pacing data for baseline example in which no block exists in the LV between the LV electrodes

| Pacing electrode | AT(1) ms | AT(2,3) ms | AT(4) ms | ED ms |
|---|---|---|---|---|
| LV1 | 0 | 25 | 50 | 50 |
| LV2 or LV3 | 25 | 0 | 25 | 50 |
| LV4 | 50 | 25 | 0 | 50 |

A second example involves an anatomic block (e.g. a scar) located in the LV tissue between LV1 and LV2. As in the first example, the same order of activation times generated during intrinsic rhythm is applied here. Since the order of activation times during intrinsic rhythm is known, ED data generation is calculated according to the previously discussed biventricular pacing configurations. In order to determine the ED data, processor 80 selects LV1 to deliver pacing pulses to LV tissue while the RV electrode paces the RV. Activation times were measured at the LV electrodes in response to the biventricular pacing configuration. AT(1) is equal to zero since LV1 is used to pace the LV. Activation times were measured at LV2, LV3 and LV4. AT(2,3) was measured at 120 ms, and AT(4) at the LV4 was measured at 110 ms. The ED at LV1 is calculated as follows:

ED(1)=AT(1)+AT(2,3)+AT(4)/2=0+120+110/2=175 ms

LV2 and/or LV3 is selected to transmit pacing pulses to LV tissue. Electrical activation times were measured at electrodes LV2, LV3 and LV4. AT(2,3) is nearly equal to zero in this case (e.g. 5 ms) since LV3 is very close to LV2 and the tissue between LV2 and LV3 conducts normally. AT(1) was measured at 120 ms while AT(4) was measured at 25 ms. The ED at LV2 is 150 ms and is calculated as follows:

ED(2 or 3)=AT(1)+AT(2,3)+AT(4)=(120+5+25) ms=150 ms

LV4 is then selected to pace the LV while the RV electrode paces the RV. In response to LV4 transmitting pacing pulses to LV tissue, electrical activation times were measured at LV1, LV2 or LV3. The AT(4) is equal to zero because LV4 is used to pace the LV. AT(1) at the LV1 was measured at 120 ms, and AT(2,3) at LV electrodes 2,3 was measured at 25 ms. The ED at LV2 is 85 ms and is calculated as follows:

ED(4)=AT(1)12+AT(2,3)+AT(4)=(120/2+25+0) ms=85 ms

LV4, physically located farthest from the anatomic block, produces an ED value that is less than the ED values of the other three LV electrodes by more than 15 ms. LV4 is the best or optimal LV electrode from which to pace the LV. Table 2 summarizes pacing data that was obtained in which an anatomic block such as a scar exists in the LV tissue between LV1 and LV2.

Table 2 summarizes pacing data for example 2 in which an anatomic block exists between LV1 and LV2

| Pacing electrode | AT(1) ms | AT(2,3) ms | AT(4) ms | ED ms |
|---|---|---|---|---|
| LV1 | 0 | 120 | 110 | 175 |
| LV2 or LV3 | 120 | 5 | 25 | 150 |
| LV4 | 120 | 25 | 0 | 85 |

A third example involves an anatomic block (e.g. a scar) located in the tissue between electrodes LV2 and LV3. Each biventricular pacing configuration is evaluated to generate ED data.

LV1 is selected to deliver pacing pulses to the LV while the RV electrode simultaneously delivers pacing pulses to the RV. In response to biventricular pacing, activation times were measured at LV2, LV3 and LV4. AT(1) is equal to zero since LV1 is used to pace the LV. AT(2) was measured at 25 ms, and AT(3) at LV3 was measured at 125 ms. Therefore, AT(2,3)= [(25+125)/2]ms=75 ms and AT(4) is 100 ms. The ED at LV1 is calculated as follows:

ED(1)=AT(1)+AT(2,3)+AT(4)/2=0+75+100/2=125 ms

LV2 is then paced while the RV electrode paces the RV. The AT(2) is zero since LV2 is used to pace the LV. In response to biventricular pacing, electrical activation times were measured at LV1, LV3 and LV4. AT(1) was measured at 25 ms, AT(3) at the LV3 was measured at 125 ms, and AT(4) at the LV4 was measured at 100 ms. AT(2,3)=(0+125)/2=62.5 ms. The ED at LV2 is 187.5 ms and is calculated as follows:

ED(2)=AT(1)+AT(2,3)+AT(4)=(25+62.5+100) ms=187.5 ms

LV3 is then paced while the RV electrode simultaneously paces the RV. AT(3) is zero since LV3 is used to pace the LV. In response to LV3 transmitting pacing pulses to LV tissue, AT were measured at LV1, LV2, and LV4. AT(1) was measured at 100 ms, AT(2) was measured at 125 ms, and AT(4) was measured at 25 ms. The ED at LV3 is calculated as follows:

ED(3)=AT(1)+AT(2,3)+AT(4)=(100+62.5+25) ms=187.5 ms

LV4 is then selected to deliver pacing pulses to the LV while the RV electrode paces the RV. The AT(4) is zero since LV4 is used to pace the LV. Activation times were measured at LV1, LV2, and LV3. AT(1) was measured at 100 ms, AT(2) is 125 ms, and AT(3) was measured at 25 ms. AT(2,3)=75 ms since AT(2,3)=(125+25)ms/2=150 ms/2. The ED at LV4 is calculated as follows:

ED(4)=AT(1)/2+AT(2,3)+AT(4)=(100/2+75+0) ms=125 ms

The pattern of electrical activation is more favorable for LV1 and LV4 since ED(1)=ED(4). LV1 is selected for pacing the LV since the tissue near LV1 exhibits the latest activation time during intrinsic activation or RV only pacing. Table 3, presented below, shows the pacing data for the anatomic block between LV2 and LV3.

TABLE 3 summary of the pacing data for example 3 where an anatomic block exists between LV2 and LV3

| Pacing electrode | AT(1) ms | AT(2) ms | AT(3) ms | AT(4) ms | ED ms |
| --- | --- | --- | --- | --- | --- |
| LV1 | 0 | 25 | 125 | 100 | 125 |
| LV2 | 25 | 0 | 125 | 100 | 187.5 |
| LV3 | 100 | 125 | 0 | 25 | 187.5 |
| LV4 | 100 | 125 | 25 | 0 | 125 |

Another example relates to an anatomic block (e.g. a scar) located in the LV tissue between LV3 and LV4. LV1 is selected to pace the LV while the RV electrode paces the RV. AT(1) is equal to zero since LV1 is used to pace the LV. In response to biventricular pacing, activation times were measured at LV2, LV3 and LV4. AT(2,3) was measured at 27.5 ms, and AT(4) was measured at 125 ms. ED(1) at LV1 is calculated as follows:

ED(1)=AT(1)+AT(2,3)+AT(1)/2=[0+27.5+(125/2)] ms=90 ms

LV2 or LV3 is then selected to pace the LV while the RV electrode paces the RV. The AT(2,3) is equal to 5 ms but is expected to be equal to zero since LV2 is used to pace the LV. In pacing of the LV and RV, electrical activation times were measured at LV1, LV3 and LV4. AT(1) was measured at 25 ms, and AT(4) was measured at 125 ms. The ED at LV2 is 150 ms and is calculated as follows:

ED(2)=AT(1)+AT(2,3)+AT(4)=(25+5+120)ms=150 ms

Pacing from LV3 creates an identical ED since LV2 and LV3 are closely spaced and tissue between LV2 and LV3 conduct normally. Therefore, ED(3)=150 ms.

LV4 is then selected to pace the LV while the RV electrode paces the RV. In response to biventricular pacing pulses, AT were measured at LV1, and AT(2, 3) but no activation time was measured at AT(4) since LV4 is used to pace the LV. AT(1) is 100 ms, and AT(2,3) at LV(2, 3) was measured at 122.5 ms. The ED at LV2 is 172.5 ms and is calculated as follows:

ED(4)=AT(1)/2+AT(2,3)+AT(4)=(100/2+122.5+0) ms=172.5 ms

The pacing data for this example is presented in Table 4.

TABLE 4

Summary of pacing data for example 4 in which an anatomic block (e.g. scar) exists between LV3 and LV4

| Pacing electrode | AT(1) ms | AT(2,3) ms | AT(4) ms | ED ms |
| --- | --- | --- | --- | --- |
| LV1 | 0 | 27.5 | 125 | 90 |
| LV2 or LV3 | 25 | 5 | 125 | 150 |
| LV4 | 100 | 122.5 | 0 | 172.5 |

Typically, the LV electrode that is most distal to the anatomic block achieves increased resynchronization between the LV and the RV. Accordingly, LV1 is the best electrode from which to pace. LV4 is the worst LV electrode from which to pace because LV4 completely blocks activation of the LV tissue. Additionally, pacing from LV2 or LV3 is worse than LV1.

A fifth example relates to a unidirectional functional block that exists between LV1 and LV2 while pacing from LV1 but is absent while pacing from LV2, LV3 or LV4. In response to LV1 biventricular pacing pulses being delivered to the RV and the LV, electrical activation times were measured at LV2, LV3 and LV4. The AT(1) is equal to zero since LV1 is used to pace the LV. AT2,3 was measured at 122.5 ms, and AT(4) was measured at 100 ms. The ED at LV1 is calculated as follows:

ED(1)=AT(1)+AT(2,3)+AT(4)/2=(0+100/2+122.5) ms=172.5 ms

LV2 or LV3 is then selected to pace the LV while the RV electrode paces the RV. In response to this biventricular pacing configuration, activation times were measured at electrodes 1, 3 and 4. AT(2,3) is nearly zero (e.g. 5 ms) since LV2 is used to pace the LV. AT(1) at the LV1 was measured at 25 ms, and AT(4) was measured at 25 ms. The ED at LV2 is 55 ms and is calculated as follows:

ED(2)=AT(1)+AT(2,3)+AT(4)=(25+5+25)ms=55 ms

Since LV3 is closely spaced to LV2, the tissue between LV2 and LV3 conducts normally. Therefore, pacing from LV3 creates an identical ED to LV2. Specifically, ED(3)=55 ms.

LV4 is then selected to pace the LV while the RV electrode paces the RV. In response to LV4 delivering pacing pulses to LV tissue, AT were measured at LV1, and electrodes 2, 3. The AT4 is equal to zero because LV4 is used to pace the LV. AT(1) at the LV1 was measured at 50 ms, and AT(2,3) at LV 2,3 was measured at 22.5 ms. The ED at LV2 is 47.5 ms and is calculated as follows:

$$ED(4)=AT(1)/2+AT(2,3)+AT(4)=(50/2+22.5+0)$$
$$ms=47.5 \text{ ms}$$

ED(2) or ED(3) and ED(4) are similar (i.e. less than 15 ms); therefore, LV2 or LV3 can be selected to pace the LV since each of these electrodes are associated with an activation times that are later than LV4. The pacing data for anatomic block between LV3 and LV4 is presented in Table 5.

TABLE 5

Summary of the pacing data for example 5 in which an anatomic block exists between LV3 and LV4

| Pacing electrode | AT(1) ms | AT(2,3) ms | AT(4) ms | ED ms |
|---|---|---|---|---|
| LV1 | 0 | 122.5 | 100 | 172.5 |
| LV2 or LV3 | 25 | 5 | 25 | 55 |
| LV4 | 50 | 22.5 | 0 | 47.5 |

The sixth example relates to LV4 that is located in or on scarred LV tissue that does not capture. In the first biventricular pacing configuration, LV1 is used to pace the LV. AT(1) is equal to zero since LV1 is used to pace the LV. In response to LV1 delivering pacing pulses to LV tissue, activation times were measured at LV2, LV3 and LV4. AT(2,3) at the LV2 was measured at 25 ms, and AT(4) was measured at 150 ms. The ED at LV1 is calculated as follows:

$$ED(1)=AT(1)+AT(2,3)+AT(4)/2=[0+25+(150/2)]$$
$$ms=100 \text{ ms}$$

LV2 or LV3 are then paced. In response to LV2 or LV3, transmitting pacing pulses to LV tissue, electrical activation times were measured at LV1, LV3 and LV4. AT(2,3) is nearly zero (e.g. 5 ms) since LV2 is used to pace the LV. AT(1) was measured at 25 ms, and AT(4) was measured at 150 ms. The ED at LV2 is 180 ms and is calculated as follows:

$$ED(2)=AT(1)+AT(2,3)+AT(4)=(25+5+150)ms=180$$
$$ms$$

Since LV3 is closely spaced to LV2, and tissue between LV2 and LV3 conducts normally and ED(3)=ED(2)=180 ms.

Table 6, presented below, summarizes all the data obtained from the examples 1-5.

TABLE 6

Summary of pacing data related to anatomic blocks in LV tissue

| Scenario | Pacing electrodes | AT(1) Milliseconds (ms) | AT (2, 3) ms | AT (3) ms | AT (4) ms | ED ms |
|---|---|---|---|---|---|---|
| Scenario 1 (baseline) No block between electrodes | LV 1 and RV electrode | 0 | 25 ms | | 50 | 50 |
| | LV 2 or LV3 and RV electrode | 25 | 5 | | 25 | 55 |
| | LV 4 and RV electrode | 50 | 25 | | 0 | 50 |
| Scenario 2 Anatomic block located in the tissue between electrodes 1 and 2 | LV 1 and RV electrode | 0 | 120 | | 110 | 175 |
| | LV 2 and RV electrode | 120 | 5 | | 25 | 150 |
| | LV 4 and RV electrode | 120 | 25 | | 0 | 85 |
| Scenario 3 Anatomic block located in the tissue between electrodes LV electrodes 2 and 3 | LV 1 and RV electrode | 0 | 25 | 125 | 100 | 125 |
| | LV 2 and RV electrode | 25 | 0 | 125 | 100 | 187.5 |
| | LV 3 and RV electrode | 100 | 125 | 0 | 25 | 187.5 |
| | LV 4 and RV electrode | 100 | 125 | 25 | 0 | 125 |
| Scenario 4 Anatomic block located in the tissue between electrodes LV electrodes 3 and 4 | LV 1 and RV electrode | 0 | 27.5 | | 125 | 90 |
| | LV 2 and RV electrode | 25 | 5 | | 125 | 150 |
| | LV 4 and RV electrode | 100 | 122.5 | | 0 | 172.5 |
| Scenario 5 Unidirectional functional block between 1 and 2 while pacing from 1 but absent while pacing from 2(3) or 4 | LV 1 and RV electrode | 0 | 122.5 | | 100 | 172.5 |
| | LV 2 and RV electrode | 25 | 5 | | 25 | 55 |
| | LV 4 and RV | 50 | 22.5 | | 0 | 47.5 |

While the five examples presented above employed a quadripolar lead with the previously specified inter-electrode distances, skilled artisans appreciate that the same principle of weighted electrical dyssynchrony measures could be applied with different weighted values different inter-electrode spacings on a lead. The weighted values are modified according to the relative distances of each electrode from the pacing electrode. For example, if the LV electrodes on a LV lead are all equidistant, then formula for the weighted electrical dyssynchrony would be modified as follows:

$$ED(1)=AT(1)+AT(2)+AT(3)/2+AT(4)/3$$

$$ED(2)=AT(1)+AT(2)+AT(3)+AT(4)/2$$

$$ED(3)=AT(1)/2+AT(2)+AT(3)+AT(4)/2 \text{ and}$$

$$ED(4)=AT(1)/3+AT(2)/2+AT(3)+AT(4).$$

Figure 7:
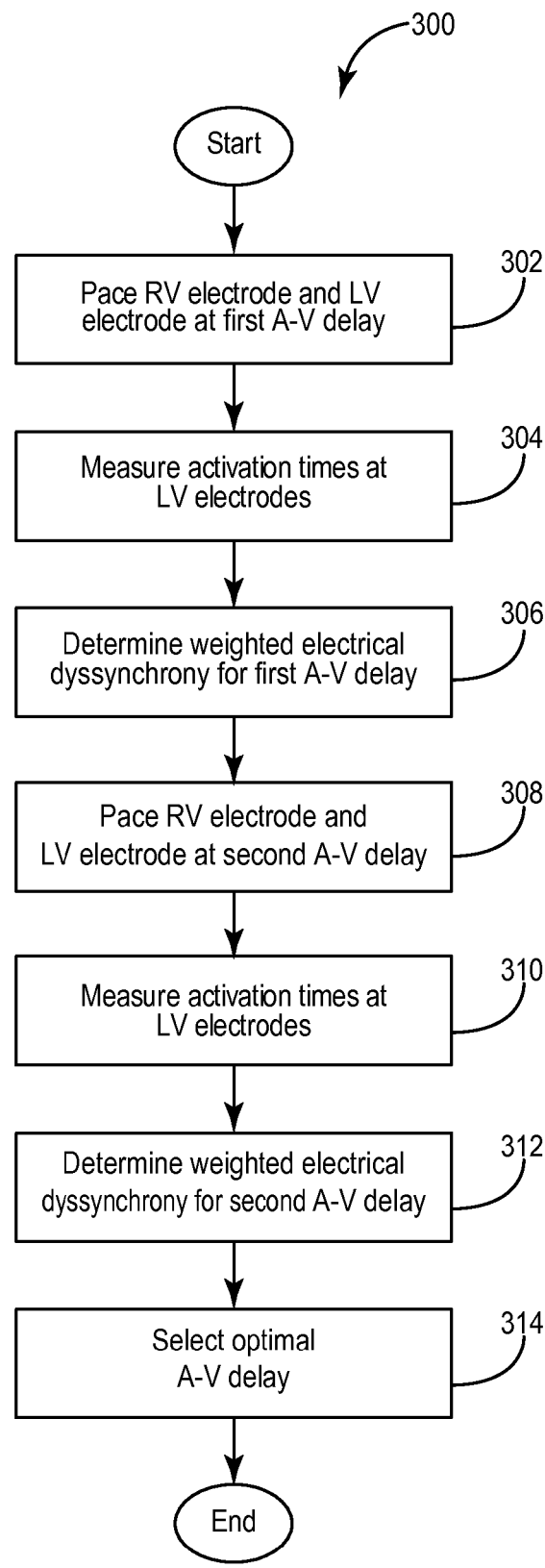
FIG. 7 is a general flow chart of an exemplary method that involves determining a weighted electrical dyssynchrony without a baseline for selecting an optimal A-V delay.
Figure 8:
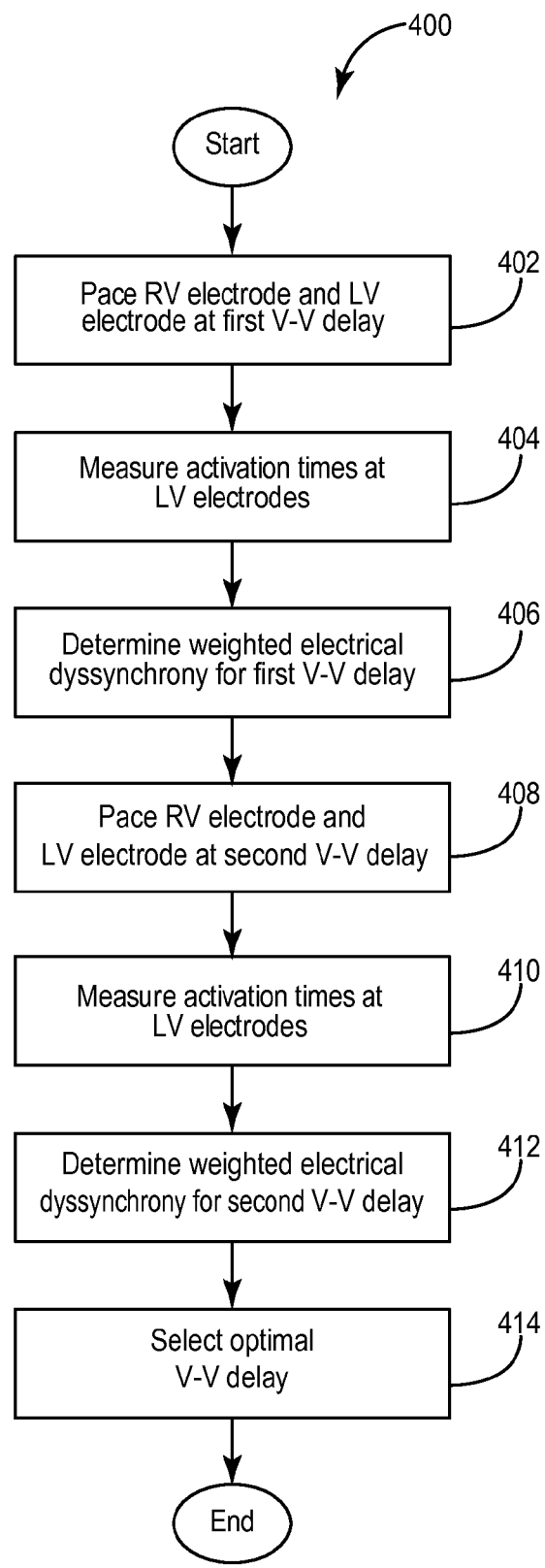
FIG. 8 is a general flow chart of an exemplary method that involves determining a weighted electrical dyssynchrony without a baseline for selecting an optimal V-V delay.

In one or more embodiments, once an optimal LV electrode is chosen, an optimal delay such as A-V delay (A) and/or V-V delay (D) can be determined through exemplary methods 300 or 400 presented in flow diagrams of FIGS. 7-8, respectively.

In one or more embodiments, once an optimal LV electrode is chosen, an optimal A-V delay can be determined through an exemplary method 300 presented in flow diagrams of FIG. 7, respectively. In one or more embodiments, A-V delay optimization occurs in a similar manner as that which was performed to select the optimal LV electrode from which to pace. In one or more embodiments, A-V delay optimization can be performed through a use of a weighted sum of activation times for various A-V delays. The A-V delay that results in the lowest electrical dyssynchrony is selected and programmed into the programmer 24.

In order to determine the optimal A-V delay, an ED must be calculated for at least two or more A-V delays with a nominal value of V-V delay D. For example, D can be set to 0. Thereafter, ED(j, A) represents the electrical dyssynchrony during simultaneous biventricular pacing from RV electrode and LV electrode j. "A" represents an A-V delay and AT(i, A) represents activation time at LV electrode i during biventricular pacing.

ED that includes a A-V delay $$ED(j,A) = \Sigma_{i=1}^{n} w(i,j) AT(i,A)$$

"n" is the total number of LV electrodes.
D is zero for the present example; however, skilled artisans appreciate that alternative embodiments are contemplated in which the V-V delay (D) is non-zero. Generally, as long as V-V delay is fixed at a constant value (e.g. zero, nonzero, nominal value), an optimal A-V delay can be adequately determined.

As previously stated, only valid ED are used to determine an optimal LV electrode from which to pace. Negative values for one or more AT(i) or values in which either LV or RV or both LV and RV do not capture are omitted. The programmer 24 can automatically choose A-V delays ranging from a lowest value of 40 ms to a highest value of 260 ms, in increments of 5, 10, 15 or 20 ms for atrial sensing. The same values are also selected during atrial pacing.

After selecting the A-V delays, the programmer 24 causes the pulse generator to generate pacing pulses (e.g. ranging from about 0.25 volts to about 8 volts and more preferably, between 2-3 volts) that are delivered through the optimal LV electrode to the LV while other pacing pulses (e.g. ranging from about 0.25 volts to about 8 volts and more preferably, between 2-3 volts) are transmitted through the RV electrode to the RV at operation 302. The physiological response to the pacing pulses can be observed.

After measuring the electrical activation times at non-pacing electrodes at operation 304, the microprocessor 80 determines electrical dyssynchrony index for the first A-V delay using the ED equation above associated with the optimal LV pacing electrode at operation 306. For example, the weighted sum equation could take into account the physical spacing, as previously discussed, between the LV electrodes on the LV lead 20. For example, the electrical dyssynchrony metric for simultaneous biventricular pacing from RV and LV1 electrode at a A-V delay of 40 ms can be expressed as follows:

$$ED(1,40) = AT(1,40) + AT([2,3],40) + AT(4,40)/2$$
wherein $AT([2,3],40) = [AT(2,40) + AT(3,40)]/2$ Since LV2 and LV3 are substantially close, the AT of LV2 and LV3 are averaged together. The AT associated with LV4 is muliplied by a constant number w(i, j). W(i, j) is a weighing factor that depends on the distance from LV1 to LV4 as compared to the distance between LV electrodes (2,3) and LV1. In this example, w(4,1) is ½ since the distance from LV1 to LV4 is twice as long as distance from electrodes (2,3) to LV1. W(i, j) can be adjusted depending upon the LV medical electrical lead and the spacing used between the plurality of electrodes thereon.

The ED equation that is used to calculate the weighted electrical dyssynchrony index for a given value A-V delay depends on the optimal LV electrode that is selected. For example, if LV1 is the optimal LV electrode, then ED(1) is used to calculate the ED for each of the A-V delays that are being tested. If LV2 is the optimal LV electrode then ED(2) is used to calculate and optimize the A-V delay. If LV3 is the optimal LV electrode then ED(3) is used to calculate and optimize the A-V delay. If LV4 is the optimal LV electrode then ED(4) is used to calculate and optimize the A-V delay.

After an ED has been determined for the first A-V delay, the programmer 24 automatically selects a second A-V delay. Again, pacing pulses are delivered through the RV electrode and the LV electrode at a second A-V delay while the sensing LV electrodes sense at operation 308. The activation times for the non-pacing LV electrodes are then measured for the second A-V delay at operation 310. The EDI for the second A-V delay is calculated at operation 312 using the same ED equation that was used to calculate the ED for the first A-V delay. After determining the second ED for a second A-V, the programmer 24 automatically selects a third A-V delay and then the programmer 24 sends pacing pulses to the RV electrode and/or the LV electrode. A third ED is then calculated for the third A-V delay. After the third ED is calculated, the programmer 24 automatically calculates up to N number of A-V delays. Typically, the programmer 24 automatically tests N (e.g. N can be 12-20 etc.) number of sensed A-V delays and M number of paced A-V delays for a resting cycle-length (e.g. time (ms) between two events such as successive atrial events). Typically N equals M, although skilled artisans will understand that N does not have to be equal to M since determining ED values for sensed A-V delays is a different operation than paced A-V delays. Generally, the programmer 24 tests less than 100 A-V delays. In one or more other embodiments, programmer 24 can automatically test 20 or less A-V delays. In yet another embodiment, programmer 24 can automatically test 10 or less A-V delays. Negative A-V delays are not tested because pre-excitation of ventricles before the atrial activation is not hemodynamically optimal.

Table 7, presented below, provides an example of ED results for SA-V delays that ranges from a short delay (i.e. 40 ms) to a long delay (i.e. 260 ms). Each A-V delay is automatically separated by predetermined time increments (i.e. 20 ms) although other suitable time incremental values (e.g. 5 ms, 10 ms, 15 ms etc.) can also be used. Biventricular pacing from LV1 and RV electrodes performed using a particular A-V delay, while maintaining the V-V delay at a constant or fixed nominal value allows exemplary data to be generated for Table 7. The A-V delay that provides a minimum ED is selected as an optimal A-V delay. In this example, the optimal A-V delay is 180 ms that corresponds to a minimum ED.

TABLE 7

ED for a range of sensed A-V (SA-V) delays at resting heart rate

| | SA-V delay (ms) | | | | | | | | | | |
|---|---|---|---|---|---|---|---|---|---|---|---|
| | 40 | 60 | 80 | 100 | 120 | 140 | 160 | 180 | 200 | 220 | 240 | 260 |
| ED(ms) | 29 | 29 | 29 | 28 | 28 | 26 | 26 | 24 | 27 | 28 | 28 | 34 |

In a situation in which two or more A-V delays have the same minimum ED, the lowest A-V delay is selected as the optimal A-V delay.

To evaluate an optimal A-V delay changes during atrial pacing, atrial pacing is initiated at a rate equal to or just above the patient's resting sinus rate. Table 8 summarizes paced A-V delays (PAV) that have been computed using a similar method as that which is described relative to SAV. The optimal PAV in this case is 200 ms.

The $\Delta AV_{rest}$ is the difference between optimal PAV and optimal SAV and is noted as follows:

$$\Delta AV_{rest} = \text{optimal } PAV - \text{optimal } SAV = (200-180)\text{ms} = 20 \text{ ms}.$$

Atrial pacing can also be initiated at decreasing cycle-lengths in steps of 50 ms from the resting cycle-length. The same procedure can be repeated in order to identify the optimal PAV at each cycle-length. For example, the lowest ED is identified and then the corresponding PA-V is selected. The corresponding optimal SAV for each cycle-length may be set by subtracting $\Delta AV_{rest}$ from the optimal PAV at that cycle-length. The range of cycle-lengths covered in this manner may start from the resting cycle-length and end in the upper atrial tracking rate.

TABLE 8

ED for a range of PAV delays at atrial pacing with cycle-length equal or just above the resting heart rate

| PA-V delay (ms) | | | | | | | | | | | |
|---|---|---|---|---|---|---|---|---|---|---|---|
| 40 | 60 | 80 | 100 | 120 | 140 | 160 | 180 | 200 | 220 | 240 | 260 |

| ED (ms) | | | | | | | | | | | |
|---|---|---|---|---|---|---|---|---|---|---|---|
| 31 | 29 | 29 | 29 | 28 | 28 | 27 | 27 | 25 | 26 | 29 | 28 |

Table 9 is a look-up table of optimal PAV and SAV values for different cycle-lengths that can be used for optimal and dynamic adaptation of A-V delay corresponding to different sensed or paced cycle-lengths. In particular, A-V optimization can automatically adjust A-V delays according to changes in heart rates (e.g. faster heart or lower cycle-lengths). The programmer 24 or IMD 16 can adjust the AV delay by using the look-up table that relates cycle length, PAV and/or SAV. For example, the IMD 16 can easily adjust the AV delay (whether atrial-sensed or atrial-paced) according to the detected current cycle-length. Referring briefly to Table 9, cycle length 750 ms corresponds to a PAV of 180 ms and a SAV of 160 ms. Accordingly, the PAV can be adjusted or the SAV can be adjusted to the designated optimum levels.

Table 9 is automatically generated by the programmer 24 and stored into memory. Programmer 24, for example, can initiate atrial pacing at different rates. The optimal PAV can be determined and stored into memory for a given atrial pacing rate. The corresponding optimal SAV can be determined for the same rate by subtracting $\Delta AV_{rest}$ as previously discussed and storing the optimal SAV value for that rate.

Table 9 is a look-up table of optimal PAV and SAV for different cycle-lengths from resting (1000 ms) to upper tracking rate (500 ms)

| Cycle length (CL) (ms) | Optimum PAV (ms) | Optimum SAV (ms) |
|---|---|---|
| 1000 | 200 | 180 |
| 950 | 200 | 180 |
| 900 | 200 | 180 |
| 850 | 200 | 180 |
| 800 | 180 | 160 |
| 750 | 180 | 160 |
| 700 | 180 | 160 |
| 650 | 160 | 140 |
| 600 | 160 | 140 |
| 550 | 140 | 120 |
| 500 | 140 | 120 |

After A-V delay has been optimized, the V-V delay undergoes the optimization process. V-V optimization occurs in a similar manner as that which was performed to select the optimal LV electrode from which to pace. In one or more embodiments, V-V optimization can be performed through a use of a weighted sum of activation times for various V-V delays and the V-V that results in the lowest activation time is selected and programmed into the programmer 24.

In order to determine the optimal V-V delay, an ED must be calculated for two or more V-V delays with the A-V delay set to optimal value $A_{opt}$.

ED that includes a V-V delay such that $$ED(j, Aopt, D) = \Sigma_{i=1}^{n} w(i,j) AT(i, Aopt, D)$$

As previously stated, only valid ED are used to determine an optimal LV electrode from which to pace. Negative values for one or more AT(i) or instances where RV or LV or both RV and LV does not capture are omitted.

The first V-V delay can be any amount of delay that the programmer 24 automatically selects for a particular patient. Alternatively, the programmer 24 can be automatically set to perform increments of delays such as 5 ms delay, 10 ms, 15 ms . . . 100 ms delay etc. Generally, introducing a V-V delay can depend on the patient's physiology (e.g. age, size, gender etc.). Either a right ventricle to left ventricle delay or a left ventricle to right ventricle delay can be input in to the programmer 24 by the user. The programmer 24 can automatically begin to introduce, for example, a 80 ms delay between the right ventricle and the left ventricle.

After selecting the V-V delay, the programmer 24 causes the pulse generator to generate pacing pulses (e.g. ranging from about 0.25 volts to about 8 volts and more preferably, between 2-3 volts) that are delivered through the optimal LV electrode to the LV while other pacing pulses (e.g. ranging from about 0.25 volts to about 8 volts and more preferably, between 2-3 volts) are transmitted through the RV electrode to the RV at operation 402. The physiological response to the pacing pulses can be observed.

After measuring the electrical activation times at non-pacing electrodes at operation 404, the microprocessor 80 determines electrical dyssynchrony index for the first V-V delay using the equation above associated with the optimal LV pacing electrode at operation 406. For example, the weighted sum equation could take into account the physical spacing, as previously discussed, between the LV electrodes on the LV lead 20. For example, the electrical dyssynchrony during biventricular pacing from RV electrode and LV1 electrode, with A-V delay between atrial (sensed or paced) signal and the first ventricular pacing pulse set to the optimal value $A_{opt}$ can be expressed as follows:

$$ED(1, A_{opt}, 40) = AT(1, A_{opt}, 40) + AT([2,3], A_{opt}, 40) + AT(4, A_{opt}, 40)/2 \text{ where } AT([2,3], A_{opt}, 40) = [AT(2, A_{opt}, 40) + AT(3, A_{opt}, 40)]/2$$

Since electrodes 2 and 3 are substantially close, the AT of electrodes 2 and 3 are averaged together. The AT associated with LV4 is divided by a constant number W. W is the distance from LV1 to LV4 as compared to LV electrodes (2,3) to 1. In this example, W is 2 since the distance from LV1 to LV4 is twice as long as distance from electrode (2,3) to LV1. W can be adjusted depending upon the LV medical electrical lead and the spacing used between the plurality of electrodes thereon.

The ED equation that is used to calculate the weighted electrical dyssynchrony index for a given value V-V delay depends on the optimal LV electrode that is selected. For example, if LV1 is the optimal LV electrode, then ED(1) is used to calculate the ED for each of the V-V delays that are being tested. If LV2 is the optimal LV electrode then ED(2) is used to calculate and optimize the V-V delay. If LV3 is the optimal LV electrode then ED(3) is used to calculate and optimize the V-V delay. If LV4 is the optimal LV electrode then ED(4) is used to calculate and optimize the V-V delay.

After an ED has been determined for the first V-V delay, the programmer 24 automatically selects a second V-V delay. Again, pacing pulses are delivered through the RV electrode and the LV electrode at a second V-V delay while the sensing LV electrodes sense at operation 408. The activation times for the non-pacing LV electrodes are then measured for the second V-V delay at operation 410. The EDI for the second V-V delay is calculated at operation 412 using the same ED equation that was used to calculate the ED for the first V-V delay. After determining the second ED for a second V-V, the programmer 24 automatically selects a third V-V delay and then the programmer 24 sends pacing pulses to the RV electrode and/or the LV electrode. A third ED is then calculated for the third V-V delay. After the third ED is calculated, the programmer 24 can calculate up to N number of V-V delays. Typically, the programmer 24 will test less than 100 V-V delays. In one or more other embodiments, the programmer 24 can test 20 or less V-V delays. In yet another embodiment, the programmer 24 can test 10 or less V-V delays.

After introducing a variety of V-V delays, a V-V delay is selected that produces the least ED at operation 414. If there are more than one V-V delays that produces the least ED, then V-V delay with the minimum absolute value would be programmed into the implantable medical device as the baseline V-V delay for the patient. For example, if the two V-V delays producing the least electrical dyssynchrony index are 0ms (simultaneous biventricular pacing) and −10 ms (LV pacing ahead of RV by 10 ms), then the programmed V-V delay would be 0ms.

V-V is optimization is illustrated through scenario three presented in Table 6 in which LV1 was selected as the optimal electrode for CRT therapy based on ED values during simultaneous biventricular pacing (V-V delay=0). The ED(1) equation was used to calculate ED at various V-V delays. ED measurements can be performed by the programmer 24 during pacing from RV electrode and pacing from the optimal electrode (electrode 1) on the LV by introducing variable V-V delays from −50 ms (LV pacing 50 ms ahead of RV pacing) to +50 ms (LV pacing 50 ms after RV pacing) at intervals of 10 ms. Table 11, presented below, summarizes ED measurements (in ms) with variable V-V delays (in ms) for scenario three (summarized in Table 6) during pacing from RV electrode and pacing from the optimal LV electrode (LV1).

The minimum ED value is obtained at a V-V delay of −20 ms which is set as the optimal V-V delay for this case.

Table 11, presented below, includes exemplary data for biventricular pacing using a plurality of V-V delays.

TABLE 11

Biventricular pacing data using a set of V-V Delays

| | V-V (ms) | | | | | | | | | | |
|---|---|---|---|---|---|---|---|---|---|---|---|
| | −50 | −40 | −30 | −20 | −10 | 0 | 10 | 20 | 30 | 40 | 50 |
| ED (ms) | 162 | 151 | 135 | 105 | 110 | 125 | 125 | 130 | 146 | 155 | 150 |

Either before or after optimizing the A-V delay and the V-V delay, a determination can be made as to whether one of the leads should be repositioned. For example, after the ED data has been obtained for each LV electrode (e.g. LV1, LV2, LV3, and LV4), then the ED data can be compared to a threshold (e.g. 60 ms). In one or more embodiments, a simple criteria on the LV activation times during RV pacing or intrinsic rhythm can be used to determine if the LV lead 20 should be moved. For example, if the LV activation times are less than 60 ms, then the lead 20 should be moved or that electrode should not be paced. This simple criterion could be added to any of the above criteria for selecting a pacing vector.

While the invention has been described in its presently preferred form, it will be understood that the invention is capable of modification without departing from the spirit of the invention as set forth in the appended claims. For example, in one or more embodiments, two or more LV electrodes may be selected for multi-site pacing of the LV. An example of such a configuration may be seen with respect to U.S. Pat. No. 6,804,555 issued Oct. 12, 2004, and assigned to the assignee of the present invention, the disclosure of which is incorporated by reference in its entirety herein. Moreover, while the electrodes have been described as being able to either sense or pace, skilled artisans appreciate that other embodiments can employ electrodes that are able to both sense and pace. Additionally, many different medical electrical leads can be used to implement one or more embodiments. For example, St Jude's Quartet™ Quadripolar, left-ventricular pacing lead or Boston Scientific's EASYTRAK left ventricular pacing/sensing lead can be used.

The techniques described in this disclosure, including those attributed to the IMD 16, the programmer 24, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

Skilled artisans also appreciate that the exemplary methods presented in the flow diagrams are intended to illustrate the general functional operation of the devices described herein, and should not be construed as reflective of a specific form of software or hardware necessary to practice all of the methods described herein. It is believed that the particular form of software will be determined primarily by the particular system architecture employed in the device (e.g., IMD 16, programmer 24) and by the particular detection and therapy delivery methodologies employed by the device and/or system. Providing software and/or hardware to accomplish the described methods in the context of any modern IMD or programmer, given the disclosure herein, is within the abilities of one of skill in the art.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure. It is appreciated that the LV electrodes can be placed at locations about and/or along the LV. It is also appreciated that more than four LV electrodes can be used to monitor electrical activation times.

Furthermore, it is understood that ED is a function of multiple variables such as pacing electrode, A-V delay, and V-V delay. Optimization of ED is based on any one variable while keeping the other variables at a constant value. Additionally, other embodiments are contemplated in which a physician may optionally perform one or more operations for any methods described herein.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. For example, it is contemplated that other embodiments could use electrodes that are configured to pace and sense. Various modifications of the illustrative embodiments, as well as additional embodiments of the disclosure, will be apparent upon reference to this description.

What is claimed:

1. A method of cardiac pacing employing a right ventricular electrode and a plurality of left ventricular electrodes, comprising:
a) pacing using the right ventricular electrode and a pacing left ventricular electrode using a first A-V delay;
b) measuring activation times at other ones of the left ventricular electrodes in response to pacing the right ventricular electrode and a pacing left ventricular electrode;
c) determining a weighted electrical dyssynchrony associated with the first A-V delay;
d) pacing using the right ventricular electrode and the pacing left ventricular electrodes using a second A-V delay;
e) measuring activation times at other ones of the left ventricular electrodes the right ventricular electrode and a pacing left ventricular electrode; and
f) determining a weighted electrical dyssynchrony for the second A-V delay;
g) comparing weighted electrical dyssynchrony for the first and the second A-V delays; and
h) selecting an optimal A-V delay in response to comparing weighted electrical dyssynchrony for the first and the second A-V delays,
wherein the weighted electrical dyssynchrony is determined using $$ED(I, A, D) = \sum_{i=1}^{n} w(1, I) AT(1, A, D)$$

wherein factor $w(i, j)$ is a distance of a sensing electrode I from a pacing electrode, n is a total number of left ventricular electrodes, atrio-ventricular delay, and D is a time delay between pacing pulses in a right ventricle and a left ventricle.

2. The method of claim 1 wherein the weighted electrical dyssynchrony includes a weighting factor associated with each of the electrodes of the left ventricular electrodes, each weighting factor based on each electrode's distance from the pacing electrode.

3. The method of claim 1 further comprising:
averaging activation times associated with the first one when two or more of the left ventricular electrodes are substantially close; and
averaging activation times associated with the second one when two or more of the left ventricular electrodes are substantially close.

4. The method claim 3, wherein substantially close is within about 1.5 mm.

5. The method of claim 1 further comprising:
determining that the optimal A-V delay is associated with a lowest value of weighted electrical dyssynchrony.

6. The method of claim 5 further comprising determining that the optimal A-V delay is associated with a smallest value A-V delay if the first and second A-V delays are associated with equal values of electrical dyssynchrony.

7. The method of claim 6 further comprising:
determining a weighted electrical dyssynchrony for N number of A-V delays; and
comparing weighted electrical dyssynchrony for the N A-V delays, wherein N is any number between 2 and 100.

8. The method of claim 7 wherein the optimal A-V delay is a last remaining A-V delay that has not been eliminated out of N A-V delays.

9. The method of claim 1 further comprising:
eliminating either the first or the second A-V delays whichever A-V delay is associated with a greater value of electrical dyssynchrony.

10. The method of claim 1 further comprising:
eliminating either the first A-V delay or the second A-V delay based upon whichever A-V delay has a greater value when the weighted electrical dyssynchrony for the first and the second A-V delays are equal.

11. The method of 10 wherein the first and second A-V delay are associated with atrial sense at a resting atrial rate.

12. The method of claim 11 wherein the resting atrial rate is between about 50 to about 75 beats per minute.

13. The method of claim 10 wherein the first and second A-V delay are associated with atrial pacing performed at a rate greater than or equal to a resting atrial rate and less than or equal to a programmed atrial upper tracking rate.

14. The method of claim 13 wherein determining $\Delta AV_{rest}$ by subtracting an optimal sensed A-V delay from an optimal paced A-V delay.

15. The method of claim 14 wherein the optimal paced A-V delay is determined for each of N number of atrial pacing rates above the resting atrial rate but less than or equal to a programmed atrial upper tracking rate.

16. The method of claim 15 further comprising determining an optimal sensed A-V delay for each corresponding atrial rate.

17. The method of claim 16 wherein the optimal sensed A-V delay is determined by subtracting $\Delta AV_{rest}$ from the optimal paced A-V delay.

18. The method of claim 16 wherein number ranges from 2-100.

19. The method of claim 16 wherein a look-up table of optimal paced and sensed A-V delays for different atrial rates may be stored and paced and sensed A-V delays are adapted accordingly in response to changes in the atrial rates during subsequent delivery of cardiac resynchronization therapy.

20. A system of cardiac pacing employing a right ventricular electrode and a plurality of left ventricular electrodes, comprising:
   a) means for pacing using the right ventricular electrode and a pacing left ventricular electrode using a first A-V delay;
   b) means for measuring activation times at other ones of the left ventricular electrodes in response to pacing the right ventricular electrode and a pacing left ventricular electrode;
   c) means for determining a weighted electrical dyssynchrony associated with the first A-V delay;
   d) means for pacing using the right ventricular electrode and the pacing left ventricular electrodes using a second A-V delay;
   e) means for measuring activation times at other ones of the left ventricular electrodes the right ventricular electrode and a pacing left ventricular electrode;
   f) means for determining a weighted electrical dyssynchrony for the second A-V delay;
   g) means for comparing weighted electrical dyssynchrony for the first and the second A-V delays; and
   h) means for selecting an optimal A-V delay in response to comparing weighted electrical dyssynchrony for the first and the second A-V delays,
   wherein the weighted electrical dyssynchrony is determined using $$ED(I, A, D) = \sum_{i=1}^{n} w(1, I) AT(1, A, D)$$

wherein factor w(i, j) is a distance of a sensing electrode I from a pacing electrode, n is a total number of left ventricular electrodes, atrio-ventricular delay, and D is a time delay between pacing pulses in a right ventricle and a left ventricle.

21. The system of claim 20 wherein the weighted electrical dyssynchrony includes a weighting factor associated with each of the electrodes of the left ventricular electrodes, each weighting factor based on each electrode's distance from the pacing electrode.

22. The system of claim 21 further comprising:
   means for averaging activation times associated with the first one when two or more of the left ventricular electrodes are substantially close; and
   means for averaging activation times associated with the second one when two or more of the left ventricular electrodes are substantially close.

23. The system claim 22, wherein substantially close is within about 1.5 mm.

24. The system of claim 20 further comprising:
   means for determining that the optimal A-V delay is associated with a lowest value of weighted electrical dyssynchrony.

25. The system of claim 20 further comprising:
   means for determining that the optimal A-V delay is associated with a smallest value A-V delay if the first and second A-V delays are associated with equal values of electrical dyssynchrony.

26. The system of claim 25 further comprising:
   means for determining a weighted electrical dyssynchrony for N number of A-V delays; and
   means for comparing weighted electrical dyssynchrony for the N A-V delays,
   wherein N is any number between 2 and 100.

27. The system of claim 26 wherein the optimal A-V delay is a last remaining A-V delay that has not been eliminated out of N A-V delays.

28. The system of claim 27 wherein the optimal sensed A-V delay is determined by subtracting $\Delta AV_{rest}$ from the optimal paced A-V delay.

29. The system of claim 26 determining an optimal sensed A-V delay for each corresponding atrial rate.

30. The system of claim 26 wherein N number ranges from 2 to about 100.

31. The system of claim 26 wherein a look-up table of optimal paced and sensed A-V delays for different atrial rates may be stored and paced and sensed A-V delays are adapted accordingly in response to changes in the atrial rates during subsequent delivery of cardiac resynchronization therapy.

32. The system of claim 25 wherein the optimal paced A-V delay is determined for each of N number of atrial pacing rates above the resting atrial rate but less than or equal to a programmed atrial upper tracking rate.

33. The system of claim 20 further comprising:
   means for eliminating either the first or the second A-V delays whichever A-V delay is associated with a greater value of electrical dyssynchrony.

34. The system of claim 20 further comprising:
   means for eliminating either the first A-V delay or the second A-V delay based upon whichever A-V delay has a greater value when the weighted electrical dyssynchrony for the first and the second A-V delays are equal.

35. The system of 20 wherein the first and second A-V delay are associated with atrial sense at a resting atrial rate.

36. The system of claim 35 wherein the resting atrial rate is between about 50 to about 75 beats per minute.

37. The system of claim 35 wherein the first and second A-V delay are associated with atrial pacing performed at a rate greater than or equal to a resting atrial rate and less than or equal to a programmed atrial upper tracking rate.

38. The system of claim 37 wherein determining $\Delta AV_{rest}$ by subtracting an optimal sensed A-V delay from an optimal paced A-V delay.

39. A method of cardiac pacing employing a right ventricular electrode and a plurality of left ventricular electrodes, comprising:

a) pacing using the right ventricular electrode and a pacing left ventricular electrode using a first A-V delay;
b) measuring activation times at other ones of the left ventricular electrodes in response to pacing the right ventricular electrode and a pacing left ventricular electrode;
c) determining a weighted electrical dyssynchrony associated with the first A-V delay;
d) pacing using the right ventricular electrode and the pacing left ventricular electrodes using a second A-V delay;
e) measuring activation times at other ones of the left ventricular electrodes the right ventricular electrode and a pacing left ventricular electrode; and
f) determining a weighted electrical dyssynchrony for the second A-V delay;
g) comparing weighted electrical dyssynchrony for the first and the second A-V delays;
h) selecting an optimal A-V delay in response to comparing weighted electrical dyssynchrony for the first and the second A-V delays, wherein the weighted electrical dyssynchrony includes a weighting factor associated with each of the electrodes of the left ventricular electrodes, each weighting factor based on each electrode's distance from the pacing electrode, wherein the weighted electrical dyssynchrony is determined using $$ED(I, A, D) = \sum_{i=1}^{n} w(1, I)AT(1, A, D)$$

wherein factor $w(i, j)$ is a distance of a sensing electrode I from a pacing electrode, n is a total number of left ventricular electrodes, atrio-ventricular delay, and D is a time delay between pacing pulses in a right ventricle and a left ventricle.

40. The method of claim 39 further comprising:
averaging activation times associated with the first one when two or more of the left ventricular electrodes are substantially close; and
averaging activation times associated with the second one when two or more of the left ventricular electrodes are substantially close.

41. The method of claim 40 where substantially close being within 1.5 mm.

* * * * *